(12) United States Patent
Sant

(10) Patent No.: US 10,307,513 B2
(45) Date of Patent: Jun. 4, 2019

(54) BIOMIMETIC HYDROGEL SCAFFOLDS AND RELATED METHODS

(71) Applicant: University of Pittsburgh—Of the Commonwealth System of Higher Education, Pittsburgh, PA (US)

(72) Inventor: Shilpa Sant, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 78 days.

(21) Appl. No.: 15/179,505

(22) Filed: Jun. 10, 2016

(65) Prior Publication Data

US 2016/0361464 A1 Dec. 15, 2016

Related U.S. Application Data

(60) Provisional application No. 62/174,813, filed on Jun. 12, 2015.

(51) Int. Cl.
| | |
|---|---|
| *A61K 9/00* | (2006.01) |
| *A61L 27/54* | (2006.01) |
| *A61L 27/26* | (2006.01) |
| *A61K 47/36* | (2006.01) |
| *A61K 47/02* | (2006.01) |
| *A61K 38/18* | (2006.01) |
| *A61L 27/52* | (2006.01) |
| *A61K 33/42* | (2006.01) |
| *A61L 27/44* | (2006.01) |
| *A61L 27/46* | (2006.01) |

(52) U.S. Cl.
CPC ............ *A61L 27/54* (2013.01); *A61K 9/0024* (2013.01); *A61K 33/42* (2013.01); *A61K 38/18* (2013.01); *A61K 47/02* (2013.01); *A61K 47/36* (2013.01); *A61L 27/26* (2013.01); *A61L 27/443* (2013.01); *A61L 27/46* (2013.01); *A61L 27/52* (2013.01); *A61L 2300/112* (2013.01); *A61L 2300/252* (2013.01); *A61L 2300/414* (2013.01); *A61L 2430/02* (2013.01); *A61L 2430/30* (2013.01); *A61L 2430/32* (2013.01)

(58) Field of Classification Search
None
See application file for complete search history.

(56) References Cited

U.S. PATENT DOCUMENTS

| | | | | |
|---|---|---|---|---|
| 4,915,839 | A * | 4/1990 | Marinaccio | B01D 39/14 210/500.23 |
| 6,699,501 | B1 * | 3/2004 | Neu | A61K 9/5089 424/450 |
| 2004/0038007 | A1 * | 2/2004 | Kotov | B01D 67/0079 428/174 |
| 2006/0175193 | A1 * | 8/2006 | Inganas | C12Q 1/6825 204/242 |
| 2006/0199273 | A1 * | 9/2006 | Rabe | B82Y 5/00 436/174 |
| 2010/0110652 | A1 * | 5/2010 | Takane | C09J 9/02 361/783 |
| 2017/0204287 | A1 * | 7/2017 | Schlenoff | C09D 201/02 |

OTHER PUBLICATIONS

Addadi, L. et al., "On how proteins interact with crystals and their effect on crystal formation", Zeitschrift für Kardiologie, 2001, pp. 92-98, vol. 90, No. 3.
Beniash, E., "Biominerals—hierarchical nanocomposites: the example of bone", Wiley Interdisciplinary Reviews: Nanomedicine and Nanobiotechnology, 2011, pp. 47-69, vol. 3, No. 1.
Berzina-Cimdina, L. et al., Research of Calcium Phosphates Using Fourier Transform Infrared Spectroscopy, Infrared Spectroscopy—Materials Science, Engineering and Technology, 2012, InTech, Chapter 6, pp. 123-148.
Boskey, A.L., "Biomineralization: Conflicts, Challenges, and Opportunities", Journal of Cellular Biochemistry Supplement, 1998, pp. 83-91, vols. 30-31.
Boskey, A.L., "Mineral Analysis Provides Insights into the Mechanism of Bbiomineralization", Calcified Tissue International, 2003, pp. 533-536, vol. 72, No. 5.
Chapman, J.A., "The Staining Pattern of Collagen Fibrils: I. An analysis of electron micrographs", Connective Tissue Research, 1974, pp. 137-150, vol. 2.
Chapman, J.A. et al., "The Staining Pattern of Collagen Fibrils: II. A comparison with patterns computer-generated from the amino acid wequence", Connective Tissue Research, 1974, pp. 151-159, vol. 2.
Chen, L. et al., "Refinement of collagen-mineral interaction: A possible role for osteocalcin in apatite crystal nucleation, growth and development", Bone, 2015, pp. 7-16, vol. 71.
Coutinho, D.F. et al., "Modified Gellan Gum hydrogels with tunable physical and mechanical properties", Biomaterials, Oct. 2010, pp. 7494-7502, vol. 31, No. 29.
Coutinho, D.F. et al., "Microfabricated photocrosslinkable polyelectrolyte-complex of chitosan and methacrylated gellan gum", Journal of Materials Chemistry, 2012, pp. 17262-17271, vol. 22, No. 33.
Dahl, T. et al., "Type I Collagen-Phosphophoryn Interactions: Specificity of the Monomer-Monomer Binding", Journal of Structural Biology, 1998, pp. 162-168, vol. 123.
Deshpande, A.S. et al., "Bio-inspired Synthesis of Mineralized Collagen Fibrils", Crystal Growth & Design, 2008, pp. 3084-3090, vol. 8, No. 8.

(Continued)

*Primary Examiner* — Susan T Tran
(74) *Attorney, Agent, or Firm* — The Webb Law Firm

(57) ABSTRACT

Provided herein are methods of making a biomimetic hydrogel scaffold comprising a polycation and a polyanion. Also provided are anisotropic biomimetic hydrogel scaffold compositions suitable for use in tissue growth, including bone, muscle, and nerve growth an optionally comprising a carbon allotrope such as graphene. Also provided are methods of producing tissue comprising growing tissue on the biomimetic hydrogel scaffold comprising a polycation and a polyanion.

24 Claims, 20 Drawing Sheets
Specification includes a Sequence Listing.

(56) References Cited

OTHER PUBLICATIONS

Ding, X. et al., "Graphene-Based Materials in Regenerative Medicine", Advanced Healthcare Materials, 2015, pp. 1451-1468, vol. 4.
Gaharwar, A.K. et al., "Bioactive Silicate Nanoplatelets for Osteogenic Differentiation of Human Mesenchymal Stem Cells", Advanced Materials, 2013, pp. 3329-3336, vol. 25.
Ganss, B. et al., "Bone Sialoprotein", Critical Reviews in Oral Biology & Medicine, 1999, pp. 79-98, vol. 10, No. 1.
Goenka, S. et al., "Graphene-based nanomaterials for drug delivery and tissue engineering", Journal of Controlled Release, 2014, pp. 75-88, vol. 173.
Kawashita, M. et al., "Apatite-forming ability of carboxyl group-containing polymer gels in a simulated body fluid", Biomaterials, 2003, pp. 2477-2484, vol. 24.
Kawska, A. et al., "The Nucleation Mechanism of Fluorapatite-Collagen Composites: Ion Association and Motif Control by Collagen Proteins", Angewandte Chemie International Edition, 2008, pp. 4982-4985, vol. 47.
Kokubo, T.,"Bioactive glass ceramics: properties and applications", Biomaterials, 1991, pp. 155-163, vol. 12.
Kokubo, T. et al., "How useful is SBF in predicting in vivo bone bioactivity?", Biomaterials, 2006, pp. 2907-2915, vol. 27.
Koutsopoulos, S., "Synthesis and characterization of hydroxyapatite crystals: A review study on the analytical methods", Journal of Biomedical Material Research, 2002, pp. 600-612, vol. 62.
Lala, S. et al., "Biocompatible nanocrystalline natural bonelike carbonated hydroxyapatite synthesized by mechanical alloying in a record minimum time", Materials Science & Engineering C, 2014, pp. 647-656, vol. 42.
Landis, W.J., "An Overview of Vertebrate Mineralization with Emphasis on Collagen-Mineral Interaction", Gravitational and Space Biology Bulletin, 1999, pp. 15-26, vol. 12, No. 2.
Landis, W.J. et al., "The structure and function of normally mineralizing avian tendons", Comparative Biochemistry and Physiology Part A, 2002, pp. 1135-1157, vol. 133.
Landis, W.J. et al., "Mineral Deposition in the Extracellular Matrices of Vertebrate Tissues: Identification of Possible Apatite Nucleation Sites on Type I Collagen", Cells Tissues Organs, 2009, pp. 20-24, vol. 189.
Mann, S. et al., "Biomineralization: Structural Questions at All Length Scales", Journal of Structural Biology, 1999, pp. 179-181, vol. 126.
Nudelman, F. et al., "Biomineralization as an Inspiration for Materials Chemistry", Angewandte Chemie International Edition, 2012, pp. 6582-6596, vol. 51.
Nudelman, F. et al., "In vitro models of collagen biomineralization", Journal of Structural Biology, 2013, pp. 258-269, vol. 183.
Nuttelman, C.R. et al., "Attachment of fibronectin to poly(vinyl alcohol) hydrogels promotes NIH3T3 cell adhesion, proliferation, and migration", Journal of Biomedical Research Materials, 2001, pp. 217-223, vol. 57, No. 2.
Olszta, M.J. et al., "Scanning Electron Microscopic Analysis of the Mineralization of Type I Collagen via a Polymer-Induced Liquid-Precursor (PILP) Process", Calcified Tissue International, 2003, pp. 583-591, vol. 72.
Ottani, V. et al., "Collagen structure and functional implications", Micron, 2001, pp. 251-260, vol. 32.
Pishbin, F. et al., "Electrophoretic Deposition of Gentamicin-Loaded Bioactive Glass/Chitosan Composite Coatings for Orthopaedic Implants", American Chemical Society Applied Materials & Interfaces, 2014, pp. 8796-8066, vol. 6.
Rabanel, J.M. et al., "Polysaccharide Hydrogels for the Preparation of Immunoisolated Cell Delivery Systems, Polysaccharides for Drug Delivery and Pharmaceutical Applications", 2006, Chapter 16, pp. 305-339.
Silver, F.H. et al., "Molecular Basis for Elastic Energy Storage in Mineralized Tendon", Biomacromolecules, 2001, pp. 750-756, vol. 2.
Silver, F.H. et al., "Deposition of apatite in mineralizing vertebrate extracellular matrices: A model of possible nucleation sites on type I collagen", Connective Tissue Research, 2011, pp. 242-254, vol. 52, No. 3.
Stetler-Stevenson, W.G. et al., "Type I Collagen Shows a Specific Binding Affinity for Bovine Dentin Phosphophoryn", Calcified Tissue International, 1986, pp. 135-141, vol. 38.
Stetler-Stevenson, W.G. et al., "Bovine Dentin Phosphophoryn: Calcium Ion Binding Properties of a High Molecular Weight Preparation", Calcified Tissue International, 1987, pp. 97-102, vol. 40.
Tamada, Y. et al., "Effect of Preadsorbed Proteins on Cell Adhesion to Polymer Surfaces", Journal of Colloid and Interface Science, 1993, pp. 334-339, vol. 155.
Tanahashi, M. et al., "Surface functional group dependence on apatite formation on self-assembled monolayers in a simulated body fluid", Journal of Biomedical Materials Research, 1997, pp. 305-315, vol. 34.
Tang, M. et al., "Enhancement of electrical signaling in neural networks on graphene films", Biomaterials, 2013, pp. 6402-6411, vol. 34.
Traub, W. et al., "Origin of Mineral Crystal Growth in Collagen Fibrils", Matrix, 1992, pp. 251-255, vol. 12.
Tzaphlidou, M., "The role of collagen in bone structure: An image processing approach", Micron, 2005, pp. 593-601, vol. 36.
Weiner, S., "Organization of Extracellularly Mineralized Tissues: A Comparative Study of Biological Crystal Growth", Critical Reviews in Biochemistry, 1986, pp. 365-408, vol. 20, No. 4.
Weiner, S. et al., "Organization of hydroxyapatite crystals within collagen fibrils", Federation of European Biochemical Societies (FEBS) Letters, 1986, pp. 262-266, vol. 206, No. 2.
Xavier, J.R. et al., "Bioactive Nanoengineered Hydrogels for Bone Tissue Engineering: A Growth-Factor-Free Approach", American Chemical Society Nano, 2015, pp. 3109-3118, vol. 9, No. 3.
Xue, Y. et al., "PEGylated poly(ester amide) elastomers with tunable physico-chemical, mechanical and degradation properties", European Polymer Journal, 2015, pp. 163-179, vol. 72.
Zhang, X. et al., "Biomimetic remineralization of demineralized enamel with nano-complexes of phosphorylated chitosan and amorphous calcium phosphate", Journal of Materials Science: Materials in Medicine, 2014, pp. 2619-2628, vol. 25.
Ziv, V. et al., "Microstructure-Microhardness Relations in Parallel-Fibered and Lamellar Bone", Bone, 1996, pp. 417-428, vol. 18, No. 5.

\* cited by examiner

SEQUENCE LISTING

```
<160> NUMBER OF SEQ ID NOS: 21

<210> SEQ ID NO 1
<211> LENGTH: 5
<212> TYPE: PRT
<213> ORGANISM: Homo sapiens

<400> SEQUENCE: 1

Ile Lys Leu Leu Ile
1               5

<210> SEQ ID NO 2
<211> LENGTH: 4
<212> TYPE: PRT
<213> ORGANISM: Homo sapiens
```

```
<400> SEQUENCE: 2

Arg Glu Asp Val
1

<210> SEQ ID NO 3
<211> LENGTH: 5
<212> TYPE: PRT
<213> ORGANISM: Homo sapiens

<400> SEQUENCE: 3

Arg Gly Asp Ser Pro
1               5

<210> SEQ ID NO 4
<211> LENGTH: 4
<212> TYPE: PRT
<213> ORGANISM: Homo sapiens

<400> SEQUENCE: 4

Arg Gly Asp Val
1

<210> SEQ ID NO 5
<211> LENGTH: 5
<212> TYPE: PRT
<213> ORGANISM: Homo sapiens

<400> SEQUENCE: 5

Leu Arg Gly Asp Asn
1               5

<210> SEQ ID NO 6
<211> LENGTH: 4
<212> TYPE: PRT
<213> ORGANISM: Homo sapiens

<400> SEQUENCE: 6

Arg Gly Asp Thr
1

<210> SEQ ID NO 7
<211> LENGTH: 5
<212> TYPE: PRT
<213> ORGANISM: Homo sapiens

<400> SEQUENCE: 7

Tyr Ile Gly Ser Arg
1               5

<210> SEQ ID NO 8
<211> LENGTH: 6
<212> TYPE: PRT
<213> ORGANISM: Homo sapiens

<400> SEQUENCE: 8

Thr Thr Ser Trp Ser Gln
1               5

<210> SEQ ID NO 9
<211> LENGTH: 8
<212> TYPE: PRT
<213> ORGANISM: Homo sapiens
```

```
<400> SEQUENCE: 9

Ala Glu Ile Asp Gly Ile Glu Leu
1               5

<210> SEQ ID NO 10
<211> LENGTH: 6
<212> TYPE: PRT
<213> ORGANISM: Homo sapiens

<400> SEQUENCE: 10

Trp Tyr Arg Gly Arg Leu
1               5

<210> SEQ ID NO 11
<211> LENGTH: 7
<212> TYPE: PRT
<213> ORGANISM: Homo sapiens

<400> SEQUENCE: 11

Ser Ile Lys Val Ala Val Ser
1               5

<210> SEQ ID NO 12
<211> LENGTH: 5
<212> TYPE: PRT
<213> ORGANISM: Homo sapiens

<400> SEQUENCE: 12

Pro Asp Ser Gly Arg
1               5

<210> SEQ ID NO 13
<211> LENGTH: 10
<212> TYPE: PRT
<213> ORGANISM: Homo sapiens

<400> SEQUENCE: 13

Arg Asn Ile Ala Glu Ile Ile Lys Asp Ile
1               5                   10

<210> SEQ ID NO 14
<211> LENGTH: 4
<212> TYPE: PRT
<213> ORGANISM: Homo sapiens

<400> SEQUENCE: 14

Asp Gly Glu Ala
1

<210> SEQ ID NO 15
<211> LENGTH: 4
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid

<400> SEQUENCE: 15

Val Thr Xaa Gly
1
```

```
<210> SEQ ID NO 16
<211> LENGTH: 6
<212> TYPE: PRT
<213> ORGANISM: Homo sapiens

<400> SEQUENCE: 16

Pro Arg Arg Ala Arg Val
1               5

<210> SEQ ID NO 17
<211> LENGTH: 19
<212> TYPE: PRT
<213> ORGANISM: Homo sapiens

<400> SEQUENCE: 17

Tyr Glu Lys Pro Gly Ser Pro Pro Arg Glu Val Val Pro Arg Pro Arg
1               5                   10                  15

Pro Gly Val

<210> SEQ ID NO 18
<211> LENGTH: 28
<212> TYPE: PRT
<213> ORGANISM: Homo sapiens

<400> SEQUENCE: 18

Arg Pro Ser Leu Ala Lys Lys Gln Arg Phe Arg His Arg Asn Arg Lys
1               5                   10                  15

Gly Tyr Arg Ser Gln Arg Gly His Ser Arg Gly Arg
            20                  25

<210> SEQ ID NO 19
<211> LENGTH: 17
<212> TYPE: PRT
<213> ORGANISM: Homo sapiens

<400> SEQUENCE: 19

Arg Ile Gln Asn Leu Leu Lys Ile Thr Asn Leu Arg Ile Lys Phe Val
1               5                   10                  15

Lys

<210> SEQ ID NO 20
<211> LENGTH: 5
<212> TYPE: PRT
<213> ORGANISM: Homo sapiens

<400> SEQUENCE: 20

Ile Lys Val Ala Val
1               5

<210> SEQ ID NO 21
<211> LENGTH: 6
<212> TYPE: PRT
<213> ORGANISM: Homo sapiens

<400> SEQUENCE: 21

Ile Lys Val Ala Val Ser
1               5
```

BIOMIMETIC HYDROGEL SCAFFOLDS AND RELATED METHODS

CROSS-REFERENCE TO RELATED APPLICATIONS

The present application claims the benefit of U.S. Provisional Application No. 62/174,813, filed Jun. 12, 2015, the contents of which are incorporated by reference herein in their entirety.

The Sequence Listing associated with this application is filed in electronic format via EFS-Web and is hereby incorporated by reference into the specification in its entirety. The name of the text file containing the Sequence Listing is 1602191_ST25.txt. The size of the text file is 4.0 KB, and the text file was created on Jun. 10, 2016.

BACKGROUND

Development of suitable, if not ideal scaffold for the regeneration of tissue is the focus of substantial research efforts. Producing a scaffold easily and inexpensively from common materials that is easy to use and that supports correct cell differentiation and growth is no trivial matter. As one example, bone has natural healing capacity but trauma due to sports or other accidents cause injuries beyond natural healing capacity. Bone cancer in children accounts for 5% of total cancers. Recent advances in biomaterials for bone regeneration have led to materials, mostly with composite or mixture of scaffolds with hydroxyapatite or other calcium phosphate nanoparticles. At best, bioactivity of the materials has been demonstrated to the induction of osteogenicity due to the degradation products of the composite scaffolds. It has been known since long that most tissues in our body has multi-scale hierarchy. Bone is formed by the deposit of inorganic minerals in an organic matrix, forming organic-inorganic nanocomposites. With clearer understanding of bone extracellular matrix (ECM) and its components, bottom-up assembly process of bone development is well studied. Bioactivity of natural bone ECM is found to be majorly due to collagen and non-collagenous proteins (NCPs). The interaction between organic matrix and minerals is considered to be the most important feature of mineralization process.

Bone loss is currently managed by filling the damaged tissue with non-bioactive and non-biodegradable materials such as metals and ceramics. They are ideal strategies for short-term management of the injury as they provide good mechanical support to maintain overall function. However, they lead to fibrotic tissue formation in the surrounding native bone due to mechanical mismatch. Moreover, different grafts are widely used for managing bone loss in clinic, however, they are limited due to complications such as graft rejection and disease transmission. The best strategy for promoting bone regeneration should be to learn from native bone development and trying to incorporate required features. Bone is composite material of organic and inorganic components. More specifically, two third of dried bone tissue in vertebrates is inorganic and the remaining one third part is composed of organic materials. Cells constitute only a small portion of total organic mass, in which collagen constitutes almost 85-90% of total organic mass. There are other components in extracellular matrix such as, acidic proteins, proteoglycans, phosphoproteins, glycoproteins and sialoproteins. Bone extracellular matrix has multiple components organized anisotropically. Characteristic self-assembly of amino acids forms triple helical structure called tropocollagen. Such self-assembly at atomic scale facilitates organization of collagen type I fibrils with overlapping and hole regions which appear as dark and light bands when observed under transmission electron microscopy (See Traub, W., T. Arad, and S. Weiner, Origin of Mineral Crystal Growth in Collagen Fibrils. Matrix, 1992. 12(4): p. 251-255).

Collagen is acknowledged as a key determinant which dictates mineralization by controlling microenvironment, mainly via charge interaction with mineral phase (See Nudelman, F., et al., In vitro models of collagen biomineralization. Journal of Structural Biology, 2013. 183(2): p. 258-269). There are several evidences (See Traub, W., T. Arad, and S. Weiner, Origin of Mineral Crystal Growth in Collagen Fibrils. Matrix, 1992. 12(4): p. 251-255; Silver. F. H. et al., Molecular Basis for Elastic Energy Storage in Mineralized Tendon, Biomacromolecules, 2001. 2(3): p. 750-756; Silver, F. H. and W. J. Landis, Deposition of apatite in mineralizing vertebrate extracellular matrices: A model of possible nucleation sites on type I collagen, Connective Tissue Research, 2011. 52(3): p. 242-254; Dahl, T., B. Sabsay, and A. Veis, Type I Collagen-Phosphophoryn Interactions: Specificity of the Monomer-Monomer Binding. Journal of Structural Biology, 1998. 123(2): p. 162-168; and Landis, W. J. and F. H. Silver, The structure and function of normally mineralizing avian tendons, Comp Biochem Physiol A Mol Integr Physiol, 2002. 133(4): p. 1135-57) which suggest that side chains of positively and negatively charged amino acids present in the light band (gap region) could provide a three dimensional microenvironment to initiate nucleation of apatite by spatially guiding calcium and phosphate ions (See Dahl, T., B. Sabsay, and A. Veis, Type I Collagen-Phosphophoryn Interactions: Specificity of the Monomer-Monomer Binding. Journal of Structural Biology, 1998. 123(2): p. 162-168; Chapman, J. A. and R. A. Hardcastle, The Staining Pattern of Collagen Fibrils: Ii. a Comparison With Patterns Computer-Generated From the Amino Acid Sequence. Connective Tissue Research, 1974. 2(2): p. 151-159; and Chapman, J. A., The Staining Pattern of Collagen Fibrils: I. an Analysis of Electron Micrographs. Connective Tissue Research, 1974. 2(2): p. 137-150). However, the precise interaction nature of collagen-mineral interaction is far from clearly understood (See Landis, W. J. and F. H. Silver, Mineral deposition in the extracellular matrices of vertebrate tissues: identification of possible apatite nucleation sites on type I collagen. Cells Tissues Organs, 2009. 189(1-4): p. 20-4). Moreover, there are other in vitro studies which suggest failure of collagen alone to interact with minerals and to create nucleation sites (See Stetler-Stevenson, W. G. and A. Veis, Bovine dentin phosphophoryn: calcium ion binding properties of a high molecular weight preparation. Calcif Tissue Int. 1987. 40(2): p. 97-102; and Stetler-Stevenson, W. G. and A. Veis, Type I collagen shows a specific binding affinity for bovine dentin phosphophoryn. Calcif Tissue Int, 1986. 38(3): p. 135-41). Additionally, conclusion of some studies advocate about NCPs (See Dahl, T., B. Sabsay, and A. Veis, Type I Collagen-Phosphophoryn Interactions: Specificity of the Monomer-Monomer Binding. Journal of Structural Biology, 1998. 123(2): p. 162-168; Stetler-Stevenson, W. G. and A. Veis, Bovine dentin phosphophoryn: calcium ion binding properties of a high molecular weight preparation. Calcif Tissue Int, 1987. 40(2): p. 97-102; Stetler-Stevenson, W. G. and A. Veis, Type I collagen shows a specific binding affinity for bovine dentin phosphophoryn. Calcif Tissue Int, 1986. 38(3): p. 135-41; and Ganss, B., R. H. Kim, and J. Sodek, Bone sialoprotein. Crit Rev Oral Biol Med, 1999. 10(1): p. 79-98) as mediators in nucleating apatite not only in gap region but also in overlap region mainly (See Deshpande. A. S. and E. Beniash, Bio-inspired Synthesis of Mineralized Collagen Fibrils. Cryst Growth Des, 2008. 8(8): p. 3084-3090). These NCPs nucleate mineral deposition with the help of interaction of functional group with calcium and phosphate ions. Therefore, structural features of collagen, either alone or along with other physicochemical factors exerted by non-collagenous proteins (NCPs) in the matrix, guide and control mineralization.

In addition to increasing interest in developing biomimetic materials, the advancement in mineralization knowledge has righteously set the new goal that the ideal material for bone regeneration will induce the same response in the body as natural bone matrix. It is important for any material intended for promoting mineralization that it develops nucleation sites similar to collagen or NCPs or both. It should also incorporate bioactive or functional molecular template which can selectively induce nucleation and provide hydrogel-like environment in which minerals can grow (See Nudelman, F. and N. A. J. M. Sommerdijk, Biomineralization as an Inspiration for Materials Chemistry. Angewandte Chemie-International Edition, 2012. 51(27): p. 6582-6596). Thus, we took up bottom up approach by designing nano-scale building blocks to shape into complex, multi-scale hierarchical structures with desired functional features for promoting mineralization. In order to maximize bioactivity of our scaffolds we strategized to incorporate both collagen stereochemistry and functional role of NCPs in nucleation and growth. Collagen-mimetic structure will provide similar structural features as steric arrangement of amino acids of tropocollagen and its charges. Such structural mimicry provides hierarchy at different length-scale, to provide the desired function in case of collagen. Along with collagen-mimetic structural features, incorporation of carboxylic and sulfate functional groups will amplify bioactivity in similar way as in NCPs and other ECM components which are also proven to be functioning as nucleators.

Regenerative approaches that employ extracellular matrix (ECM)-like materials have been explored by researchers in the last decade, however, they fail to regenerate and remodel the bone. Natural bone development mechanisms need to be facilitated in regenerative materials based therapies in order to promote proper bone regeneration (See Nudelman, F. and N. A. J. M. Sommerdijk. Biomineralization as an Inspiration for Materials Chemistry. Angewandte Chemie-International Edition, 2012. 51(27): p. 6582-6596). Many approaches employ inorganic-organic composites, a blend of synthetic minerals and natural or synthetic scaffolds which often end up using growth factors to promote bone growth due to lack of bioactivity from scaffolds.

SUMMARY

A synthetic matrix is provided that uses bioactive properties to sequester and deposit minerals from simulated body fluid into the matrix in biomimetic fashion. Moreover, an innovative and simple method is employed for fibrous scaffold fabrication. The method has potential for its use in fibrous scaffold fabrication which can employ the principle of self-assembly of oppositely charged ingredients.

In one aspect, described herein are methods and compositions that include features that facilitate interaction between organic and inorganic phase at molecular level in close similarity to that of bone. Charges work as one of the driving forces for mineral sequestration. Charge imparting groups such as carboxylate and sulfate have also been implicated as a determinant in precisely controlled mineral deposition event. To ensure bone mimicking mineral deposition, an organic matrix is assembled in as close a resemblance as in nature. One characteristic of collagen is its unique self-assembly, in which electrostatic and hydrophobic interactions drive its sophisticated hierarchy at different length scale. Amino acids self-assemble to form triple helical structure of tropocollagen which further organizes into fibrils and fiber bundles, to give hierarchy to bone at different length-scale. Animal-derived collagen is source of infections in many approaches and it is challenging to develop fibrous structures using animal derived collagen.

Provided herein are methods of producing a biotherapeutic composition, comprising feeding a first component comprising a positively-charged polyelectrolyte, and a second component comprising a negatively-charged polyelectrolyte through a fluid flow passage to produce a product comprising a anisotropic structure. In some aspects, the passage is cylindrical, and is optionally a tube or a hypodermic needle. In further aspects, the passage has a largest cross section of 10 mm or less. In some examples, the method further comprises collecting the product onto a surface, and drying the collected material to produce a sheet.

In aspects, the negatively-charged polyelectrolyte and/or the positively-charged polyelectrolyte is a polysaccharide. In some examples, the negatively-charged polyelectrolyte is one or more of gellan gum (GG) and alginate (Alg), Kappa carrageenan (KCa), hyaluronic acid (HA), chondroitin sulfate, poly(aspartic acid), and poly(glutamic acid) (PGA). Further, in some aspects the positively-charged polyelectrolyte is chosen from one or more of: chitosan, glucosamine sulfate, chondroitin sulfate, or a positively-charged peptide. In some embodiments, the positively-charged polyelectrolyte is poly-L-lysine, polycysteine, and poly-L-arginine. In aspects, the positively-charged electrolyte is chitosan. Some examples provide that the negatively-charged electrolyte is alginate, gellan gum, and/or kappa-caragenean. In some aspects, the positively-charged polyelectrolyte and/or the negatively-charged polyelectrolyte are a polyurethane, a polyester, or a polyether.

In some examples, the absolute values of the zeta potentials for the positively-charged polyelectrolyte and the negatively-charged polyelectrolyte differ by no more than 50%. In aspects, the overall average charge of the positively-charged polyelectrolyte is less than the overall average charge of the negatively-charged polyelectrolyte, yielding an aligned structure having an overall negative charge. In other aspects, the method further comprises feeding a cationic or anionic composition into the passage with the first and second components. In some examples, the cationic or anionic composition comprises $Ca^{2+}$ and/or a calcium phosphate, such as hydroxyapatite.

In some aspects, the method further comprises feeding a therapeutic agent into the passage with the first and second components. In some examples, the therapeutic agent is one or more of: an antimicrobial agent, a growth factor, a cytokine, an antioxidant, an anticancer agent, an anti-inflammatory agent, a retinoid, and a steroid. In some aspects the therapeutic agent is: basic fibroblast growth factor (bFGF), acidic fibroblast growth factor (aFGF), vascular endothelial growth factor (VEGF), hepatocyte growth factor (HGF), insulin-like growth factors 1 and 2 (IGF-1 and IGF-2), platelet derived growth factor (PDGF), stromal derived factor 1 alpha (SDF-1 alpha), nerve growth factor (NGF), ciliary neurotrophic factor (CNTF), neurotrophin-3, neurotrophin-4, neurotrophin-5, pleiotrophin protein (neurite growth-promoting factor 1), midkine protein (neurite growth-promoting factor 2), brain-derived neurotrophic factor (BDNF), tumor angiogenesis factor (TAF), corticotrophin releasing factor (CRF), transforming growth factors α and β (TGF-α and TGF-β), interleukin-8 (IL-8), granulocyte-macrophage colony stimulating factor (GM-CSF), osteopontin, osteocalcin, an interleukin, and/or an interferon. Alternatively, in some aspects, the therapeutic agent is a biologic.

In some aspects, the method further comprises feeding a carbon allotrope into the passage with the first and second components.

Provided herein are compositions comprising an anisotropic assembly of a positively-charged polyelectrolyte and a negatively-charged polyelectrolyte, optionally, having a collagen-like light and dark banding pattern, like the light and dark banding pattern of collagen. In some examples, the negatively-charged polyelectrolyte and/or the positively-charged polyelectrolyte is a polysaccharide. In other aspects, the negatively-charged polyelectrolyte is one or more of gellan gum (GG) and alginate (Alg), Kappa carrageenan (KCa), hyaluronic acid (HA), chondroitin sulfate, poly(aspartic acid), and poly(glutamic acid) (PGA). In aspects, the positively-charged polyelectrolyte is chosen from one or more of: chitosan, glucosamine sulfate, chondroitin sulfate, or a positively-charged peptide. In some aspects, wherein the positively-charged polyelectrolyte is poly-L-lysine, polycysteine, and poly-L-arginine. In aspects, the positively-charged electrolyte is chitosan. In aspects, the negatively-charged electrolyte is alginate, gellan gum, and/or kappa-carageenan. In some aspects, the positively-charged polyelectrolyte and/or the negatively-charged polyelectrolyte are a polyurethane, a polyester, or a polyether.

In some examples, the absolute values of the zeta potentials for the positively-charged polyelectrolyte and the negatively-charged polyelectrolyte differ by no more than 50%. In some aspects, the overall average charge of the positively-charged polyelectrolyte is less than the overall average charge of the negatively-charged polyelectrolyte, yielding a aligned structure having an overall negative charge. In aspects, one or both of the positively-charged polyelectrolyte and the negatively-charged polyelectrolyte is conjugated to a peptide. In some aspects, the composition is complexed with a carbon allotrope. In some aspects, the composition is complexed with a cationic composition. In some examples, the cationic composition comprises Ca2+ and/or a calcium phosphate, such as hydroxyapatite.

In some aspects, the composition is complexed with a therapeutic agent. In aspects, the therapeutic agent is one or more of: an antimicrobial agent, a growth factor, a cytokine, an antioxidant, an anticancer agent, an anti-inflammatory agent, a retinoid, a biologic, and/or a steroid. In some examples, the therapeutic agent is: basic fibroblast growth factor (bFGF), acidic fibroblast growth factor (aFGF), vascular endothelial growth factor (VEGF), hepatocyte growth factor (HGF), insulin-like growth factors 1 and 2 (IGF-1 and IGF-2), platelet derived growth factor (PDGF), stromal derived factor 1 alpha (SDF-1 alpha), nerve growth factor (NGF), ciliary neurotrophic factor (CNTF), neurotrophin-3, neurotrophin-4, neurotrophin-5, pleiotrophin protein (neurite growth-promoting factor 1), midkine protein (neurite growth-promoting factor 2), brain-derived neurotrophic factor (BDNF), tumor angiogenesis factor (TAF), corticotrophin releasing factor (CRF), transforming growth factors α and β (TGF-α and TGF-β), interleukin-8 (IL-8), granulocyte-macrophage colony stimulating factor (GM-CSF), osteopontin, osteocalcin, an interleukin, and/or an interferon.

Additionally provided herein are methods of producing a composition for use in bone mineralization, drug delivery, cell-growth and muscle tissue engineering, comprising the steps of a.) mixing a positively-charged polysaccharide and a negatively-charged polysaccharide to produce a mixture; and b.) passing the mixture through a passage of sufficient diameter and length to produce an anisotropic product. In some aspects, the positively-charged polyelectrolyte is chosen from one or more of: chitosan, glucosamine sulfate, chondroitin sulfate, or a positively-charged peptide and/or the negatively-charged polyelectrolyte is one or more of gellan gum (GG) and alginate (Alg), Kappa carrageenan (KCa), hyaluronic acid (HA), chondroitin sulfate, poly(aspartic acid), and poly(glutamic acid) (PGA).

Provided herein are methods of delivering a therapeutic agent or cell to a patient, comprising administering to the patient a composition prepared as discussed above.

Provided herein are methods of growing cells or tissue, comprising incubating, in an appropriate cell growth medium, cells placed in contact with the composition prepared as discussed above.

Provided herein are methods of making tissue, comprising feeding a first component comprising feeding a first component comprising a positively-charged polyelectrolyte, and a second component comprising a negatively-charged polyelectrolyte through a fluid flow passage to produce a product comprising a anisotropic structure. In aspects, the tissue is bone, nerve, or muscle. In some aspects, the tissue is nerve or muscle, and the method further comprises feeding a carbon allotrope into the passage with the first and second components. In other aspects, the method further comprises feeding a therapeutic agent into the passage with the first and second components.

BRIEF DESCRIPTION OF THE DRAWINGS

In FIG. 3, letter A denotes CHT-GG scaffold, letter B denotes CHT-Alg scaffold, letter C denotes CHT-KCa scaffold; number 1 denotes photographic naked eye view, number 2 denotes light microscopy, number 3 denotes Surface Electron Microscopy (SEM), number 4 denotes Transmission Electronic Microscopy (TEM); Each film consists of two layers of 45 hydrogel fibers overlaid on top of each other.

FIG. 4A shows fourier transform infrared spectroscopy (FTIR) of CHT-GG scaffold; FIG. 4B shows FTIR of CHT-Alg scaffold: FIG. 4C shows FTIR of CHT-KCa scaffold (top spectrum: mineralized scaffold, bottom spectrum: non mineralized (control) scaffold); FIG. 4D shows X-ray diffraction; top spectrum: CHT-GG SBF, middle spectrum CHT-Alg SBF, bottom spectrum: CHT-KCa SBF; gray highlighted regions are characteristic peaks that are common with Hydroxyapatite spectra; and FIG. 4E shows FTIR for commercially-available HA and ACP.

In FIG. 5A: white arrow represents scaffold, and black arrow represents minerals. In FIGS. 5A and 5B letters A and D denote CHT-GG, letters B and E denote CHT-Alg, and letters C and F denote CHT-KCa.

In FIGS. 6A-6C letters A and D denote CHT-GG, B and E denote CHT-Alg, C and F denote CHT-KCa: number 1 denotes non mineralized scaffolds (distilled water control) and number 2 denotes mineralized scaffolds (3 day incubation in simulated body fluid).

FIG. 18 shows confocal images of CHT GG control scaffolds stained with nuclei staining (Hoechst) (blue in original) and myosin heavy chain (MHC) (green in original); Panel A1 shows confocal images of 0.01% graphene CHT GG control scaffolds. Panel B1 shows confocal images for 0.05%, Panel C1 shows confocal images for 0.1% and Panel C2 shows a close-up of the boxed region in Panel C1; scale bars indicate 40 μm, n=at least 3 for each type of scaffolds.

DETAILED DESCRIPTION

Figure 1:
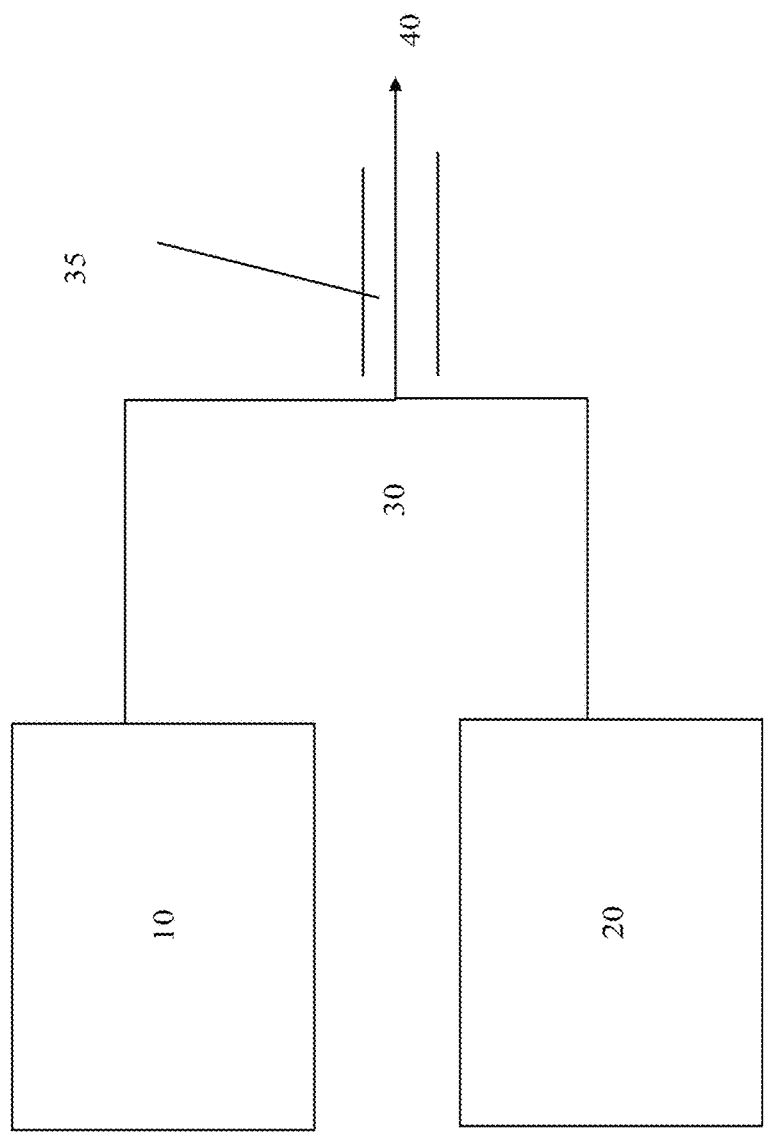
FIG. 1 shows a schematic depiction of a system for production of the method herein described.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values.

As used herein, the "treatment" or "treating" of a wound or defect means administration to a patient by any suitable dosage regimen, procedure and/or administration route of a composition, device or structure with the object of achieving a desirable clinical/medical end-point, including attracting progenitor cells, healing a wound, correcting a defect, etc.

As used herein, the terms "comprising," "comprise" or "comprised," and variations thereof, are meant to be open ended. The terms "a" and "an" are intended to refer to one or more.

As used herein, the term "patient" or "subject" refers to members of the animal kingdom including but not limited to human beings and "mammal" refers to all mammals, including, but not limited to human beings.

As described herein, a "fiber" an elongated, slender, thread-like and/or filamentous structure. A "matrix" is any two- or three-dimensional arrangement of elements (e.g., fibers), either ordered (e.g., in a woven or non-woven mesh) or randomly-arranged, and can be isotropic or anisotropic.

As described herein, a "passage" is an opening in an object comprising an inlet and an outlet through which a fluid can pass, e.g., a closed channel having a beginning and an end through which a fluid can pass. The passage may be uniform in shape over its length (longitudinal), or non-uniform, smooth or rough, circular, elliptical, or any shape in cross section, and the shape, size and surface (wall) characteristics can be different over the length of the passage. Examples of passages include pipes, tubes, and holes formed (e.g., drilled, etched, melted, or molded) through a solid object. As described below a pipe may be a hollow metal pipe such as a hypodermic needle or cannula, or a polymer tube, such as a silicone tube as are broadly-known in the medical arts. As is broadly understood in the fluid mechanics arts, fluid (gas or liquid) flow through a passage is complex, and depends, for example and without limitation, upon the rheology of the fluid passing through the passage, the smoothness or roughness of the walls of the passage, the material of the wall of the passage, and the velocity of fluid flow through the passage. A passage with a circular cross section has a diameter. A passage with a non-circular cross-section has a largest cross section, which is the largest distance between walls of the passage perpendicular to the longitudinal axis (the general direction of fluid flow) of the passage. The length of the passage is typically at least 5 times to 10 times the largest cross section of the passage, and can be greater. In the context of the methods described herein, the passage is typically cylindrical, having a circular cross section, as exemplified by the hollow hypodermic needles and tubes. A tube having an outside diameter of 6 mm (inside diameter of 4-5 mm) was able to produce the anisotropic product described herein, as was an 18 G hypodermic needle. It is therefore believed that even though passage of the components of the product described herein have to pass through a passage, the diameter, speed, pressure, and shape of the passage is less important than subjecting the mixed components of the product to the particular flow mechanics of a tube or pipe or other type of passage, including, without any intent to be bound by this theory, wall friction, turbulent flow, Reynold's number, hydraulic diameter, laminar flow, etc. In all cases, the flow rate of the liquid containing the constituents of the anisotropic product are passed through the passage at a flow rate sufficient to product an anisotropic product. Theoretically, for any particular mixture of components, at some point, the diameter or largest cross section will be too large, the shape of the passage will be incorrect, or the length of the passage will be too short to produce an aligned or anisotropic product, but one of ordinary skill can readily deduce such limits for any set of ingredients to be mixed by simple experimentation, that is by determining if the product has sufficient or insufficient anisotropy for a desired use. As such, in one aspect, the fluid flow passage is described herein as being sufficient for or able to produce an anisotropic product. In one aspect, the fluid flow passage is a cylindrical tube of 1 inch or less, 10 mm or less, 5 mm or less, or two mm or less in diameter, and optionally is at least one inch in length, for instance a 4 mm inside diameter tube, or an 18 G hypodermic needle. As one of ordinary skill can imagine, the one or more passages may be drilled or otherwise formed into a structure, such as a manifold, for ejecting one or more streams of the product, e.g., onto a surface, such as one or more xyz stages.

As used herein a polyelectrolyte is a polymeric composition having a plurality of charged groups or moieties, such that a negatively-charged polyelectrolyte comprises an overall negative charge and a plurality of negatively-charged groups or moieties, and a positively-charged polyelectrolyte comprises an overall positive charge and a plurality of positively-charged groups or moieties. A polyelectrolyte has a positive or negative charge, as the case may be, at a relevant pH, e.g., at physiological pH of approximately 7.4, or a pH range of, e.g., 6-9, 7-8, etc., at which the polyelectrolytes are assembled.

In one aspect, a method of preparing an organic matrix is provided. The method exploits the electrostatic interaction between oppositely-charged polyelectrolytes (e.g., polysaccharides) to facilitate their self-assembly. Assembly is performed while a mixture containing the polyelectrolytes are passed through a passage of a diameter and length sufficient to cause the polyelectrolytes to align, rendering an ordered, anisotropic product, e.g., with the polyelectrolyte chains in substantial alignment. That is, the product is anisotropic, e.g., the polymer chains being arranged in an ordered fashion, yielding one or more different physical property in different directions, for example having the fibers extending in generally the same direction, as opposed to random or isotropic orientation. The passage is, according to one aspect, no more than 1 inch, 10 mm, 5 mm, 4 mm, 3 mm, or 2 mm in its largest cross-section, and has a length of at least two times, and in most aspects, at least 10 times the largest cross section.

By "fluidly connected" it is meant that a contiguous passage is created between two stated elements through which a fluid can flow. Thus, medical syringe is fluidly connected to a hypodermic needle when the needle is attached to the syringe, creating a contiguous passage such that fluid can be forced from the medical syringe through the lumen of the attached needle without diversion of the fluid. Likewise, a tube attached to an outlet of a pump is fluidly connected to the pump because a contiguous passage is created by such attachment. A "reservoir" is any container that stores a substance, and includes, for example and without limitation, vials, jars, bags (e.g., an i.v. bag), syringes, bottles, cartridges, etc.).

In the method, a first component comprising a positively-charged polyelectrolyte, and a second component comprising a negatively-charged polyelectrolyte are combined and are fed through a passage of a sufficient cross section and diameter, for example, no more than 1 inch, 10 mm, 5 mm, 4 mm, 3 mm, or 2 mm in its largest cross-section, e.g., diameter, and having a length of at least two times, e.g., 10 times the largest cross section of the passage, at a flow rate sufficient to produce an anisotropic product, optionally having a banding pattern, such as dark and light bands characteristic of collagen. The passage is in one aspect, a tube, such as a metal tube or a hypodermic needle, or a piece of tubing, such as 6 mm Tygon® tubing.

As the mixture is passed through the passage, an anisotropic product is produced. The anisotropic product is deposited onto (collected on) a surface and is optionally dried. The surface and/or the passage are optionally movable in three dimensions such that deposition of the anisotropic product can be controlled in three dimensions to produce a three-dimensional shape. In one aspect, deposition of the product is spatially-controlled by a computer process, thereby printing a shape in three-dimensions. In one aspect, the surface onto which the product is deposited is a three-dimensional (xyz) stage, as are broadly-known and are commercially available. A typical system for production of the anisotropic product is depicted schematically in FIG. 1, including a first reservoir 10 containing the first component, and a second reservoir 20 containing the second component. Components of FIG. 1 are not to scale. The first and second component are pumped by pumps (not shown for clarity) from the reservoirs and are mixed 30 and passed through passage 35. Anisotropic product 40 exits passage 35.

Although the product may be dried for ease of storage and distribution, the product is used in a hydrated state. Where the product is dried after deposition, it is rehydrated prior to use, for example in water, saline, Ringer's, phosphate-buffered saline (PBS), cell culture medium, plasma, etc. For use in bone regeneration, the product is deposited at a location in a patient where bone growth is desired, for example at a site of traumatic injury or removal of bone tissue. Likewise for use in nerve regeneration or muscle regeneration, the product is placed at a site in a patient where nerve or muscle growth is desired or needed, such as a site of traumatic injury or surgical removal of the tissue.

In addition to the polyelectrolytes, according to one aspect, a third composition is fed into the passage with the first and second components (polyelectrolytes). In one aspect, the third composition is mixed with the first and/or second composition prior to mixing the first and second composition. In another aspect, it is fed by itself into the passage from an independent source from the first and second components. The third composition is a substance to be trapped within the product. In one aspect the third composition is a carbon allotrope, such as graphene. For example, as indicated below, up to 0.1% by weight (% wt) of graphene may be added to the chitosan-gellan gum product, improving the tensile strength, conductivity, and wettability of the composition, rendering it especially useful for muscle or nerve tissue growth. In one aspect, the graphene is pre-mixed with the chitosan, and then the chitosan/graphene is mixed the gellan gum and passing the mixture through the passage.

The third composition, or a fourth composition in addition to the carbon allotrope, may be a therapeutic agent, such as a growth factor or chemoattractant, as are broadly-known, for example as described below.

Additional therapeutic agents, e.g., as described below, optionally are absorbed into or adsorbed to the product in any aspect described herein. A therapeutic agent is absorbed into or adsorbed to by contacting the product according to any aspect described herein, either in a dry state or in a hydrated state (e.g. during rehydration of dried product prior to use/implantation) with the composition until a desired amount of the composition is absorbed into or adsorbed to the product.

A composition therefore is provided comprising a positively-charged polyelectrolyte and a negatively-charged polyelectrolyte. The composition is anisotropic, e.g., assembled in substantially parallel alignment and, optionally, having a banded pattern, e.g., dark and light bands, as are found in collagen. As above, in one aspect, the positively-charged and/or negatively-charged polyelectrolyte are polysaccharides.

In certain aspects or the methods and compositions described herein, polysaccharides are used as the positively-charged and/or the negatively-charged polyelectrolyte. In the example below, chitosan (CHT) was chosen as a common positive polyelectrolyte, for its proven role in mineralization process in various sea creatures, along with three different negative polyelectrolytes. In one aspect, selection of negatively charged polyelectrolyte is based on resemblance of negative charge imparting group, such as carboxyl or sulfate, with that of components of natural extracellular matrix (ECM). In the example below, gellan gum (GG) and alginate (Alg), which have carboxylate (COO—) as their negative charge imparting group, were chosen for their similarity with charge-imparting group as in hyaluronic acid. Similarly, Kappa carrageenan (KCa) was chosen for its sulfate ($SO_4^{2-}$) group being common charge imparting group with glycosaminoglycan (GAG) and chondroitin sulfate (found in ECM). Moreover, as shown in the table accompanying FIG. 2, GG and Alg differ with each other in their electrostatic charges which is anticipated to elucidate its role in mineral deposition. Three hydrogel scaffolds, described in the example below, incorporate negative charge-imparting functional group as discussed earlier. CHT-GG and CHT-Alg both have different anionic polysaccharide (GG and Alg) with same charge imparting group as carboxylate.

Additional non-limiting examples of positively-charged polymers as poly-L-lysine (PLL), glucosamine sulfate and positively-charged peptides or polyamino acids, such as PLL or Polycysteine. Non-limiting examples of additional negatively-charged polymers include: hyaluronic acid (HA), chondroitin sulfate and poly(glutamic acid) (PGA), polyaspartic acid. Criterion for selecting the polymers include having functional groups similar to that of native extracellular matrix, e.g., carboxylate and sulfate are abundant functional groups in ECM of bone. Similarly, for any other application, depending on composition of native microenvironment or ECM, various natural or synthetic polyelectrolytes can be chosen.

In terms of selecting pairs of negatively-charged and positively-charged polyelectrolytes, Zeta potential of a polyelectrolyte is one parameter to predict the self-assembly. That is, balanced positive and negative Zeta potential will be strongly predictive of self-assembly. However, if amount of positive and negative charge is not completely neutralizing (e.g., +40, −40 mV) or if it is quite different from each other (e.g., +10, −40 mV), it may still self-assemble. Parameters such as speed of both pumps can be altered to let one of the polymer flow faster than the other, and is a matter of optimization for each pair of polyelectrolytes. As used herein, the "overall average charge" refers to the absolute value of the difference between the average number of positive charges and negative charges on a compound such as a polypeptide, protein, or polysaccharide. It is understood that a population of polymer molecules has a certain degree of polydispersity, and that the average number of positive or negative charges is the mean number of positive or negative charges, respectively. Zeta potential is an art-recognized measure of the surface electrostatic potential of a particle, and is commonly measured by electrophoretic mobility using any of many commercially-available devices and measurement technologies. In one aspect, the absolute values of the zeta potentials for the positively-charged polyelectrolyte and the negatively-charged polyelectrolyte differ by no more than 50%, e.g., by no more than 10%, 20%, 25%, 30%, 40% or 50% and/or the overall average charge of the positively-charged polyelectrolyte is within 50%, e.g., within 10%, 20%, 25%, 30%, 40% or 50% of the absolute value of the average charge of the negatively-charged polyelectrolyte.

In one aspect, one or both of the polyelectrolytes are conjugated by standard methods (e.g. by NHS/EDC chemistry) to a bioactive peptide. Useful bioactive peptides include or consist of the following amino acid sequences: IKLLI (SEQ ID NO: 1) (anti-apoptotic), REDV (SEQ ID NO: 2), LDV, RGDSP (SEQ ID NO: 3), RGDV (SEQ ID NO: 4). LRGDN (SEQ ID NO: 5). RGDT (SEQ ID NO: 6), YIGSR (SEQ ID NO: 7), TTSWSQ (SEQ ID NO: 8), AEIDGIEL (SEQ ID NO: 9), WYRGRL (SEQ ID NO: 10), SIKVAVS (SEQ ID NO: 11), PDSGR (SEQ ID NO: 12). RNIAEIIKDI (SEQ ID NO: 13), DGEA (SEQ ID NO: 14). VTXG (SEQ ID NO: 15), PRRARV (SEQ ID NO: 16), YEKPGSPPREVVPRPRPGV (SEQ ID NO: 17), RPSLAK-KQRFRHRNRKGYRSQRGHSRGR (SEQ ID NO: 18), RIQNLLKITNLRIKFVK (SEQ ID NO: 19), RGD, IKVAV (SEQ ID NO: 20) and IKVAVS (SEQ ID NO: 21). In one aspect, these oligopeptides are linked via their amine groups to the polyelectrolyte structures described herein.

In certain embodiments, the composition is used for release of therapeutic agents within a patient's body. For example, at least one therapeutic agent is added to the composition described herein before it is implanted in the patient or otherwise administered to the patient, for example, a therapeutic agent is added to the described polyelectrolyte pair as a third component, as they are combined. Generally, the therapeutic agents include any substance that can be coated on, embedded into, absorbed into, adsorbed to, or otherwise attached to or incorporated onto or into the composition described herein or incorporated into a drug product that would provide a therapeutic benefit to a patient. Non-limiting examples of such therapeutic agents include antimicrobial agents, growth factors, emollients, retinoids, and topical steroids. Each therapeutic agent may be used alone or in combination with other therapeutic agents. For example and without limitation, a composition comprising neurotrophic agents or cells that express neurotrophic agents may be applied to a wound that is near a critical region of the central nervous system, such as the spine.

In certain aspects, the therapeutic agent is a growth factor, such as a neurotrophic or angiogenic factor, which optionally may be prepared using recombinant techniques. Non-limiting examples of growth factors include basic fibroblast growth factor (bFGF), acidic fibroblast growth factor (aFGF), vascular endothelial growth factor (VEGF), hepatocyte growth factor (HGF), insulin-like growth factors 1 and 2 (IGF-1 and IGF-2), platelet derived growth factor (PDGF), stromal derived factor 1 alpha (SDF-1 alpha), nerve growth factor (NGF), ciliary neurotrophic factor (CNTF), neurotrophin-3, neurotrophin-4, neurotrophin-5, pleiotrophin protein (neurite growth-promoting factor 1), midkine protein (neurite growth-promoting factor 2), brain-derived neurotrophic factor (BDNF), tumor angiogenesis factor (TAF), corticotrophin releasing factor (CRF), transforming growth factors α and β (TGF-α and TGF-β), interleukin-8 (IL-8), granulocyte-macrophage colony stimulating factor (GM-CSF), osteopontin, osteocalcin, interleukins, and interferons. Commercial preparations of various growth factors, including neurotrophic and angiogenic factors, are available from R & D Systems, Minneapolis, Minn.; Biovision, Inc, Mountain View, Calif.; ProSpec-Tany TechnoGene Ltd., Rehovot, Israel; and Cell Sciences®, Canton, Mass.

In certain aspects, the therapeutic agent is an antimicrobial agent, such as, without limitation, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxyccline, ampicillin, amphotericin B, ketoconazole, fluconazole, pyrimethamine, sulfadiazine, clindamycin, lincomycin, pentamidine, atovaquone, paromomycin, diclazaril, acyclovir, trifluorouridine, foscarnet, penicillin, gentamicin, ganciclovir, iatroconazole, miconazole, Zn-pyrithione, and silver salts such as chloride, bromide, iodide and periodate.

In one aspect, the therapeutic agent is a biologic. A "biologic" or biological product includes products such as vaccines, blood and blood components, allergenics, somatic cells, gene therapy, tissues, and recombinant therapeutic proteins, and can be composed of sugars, proteins, or nucleic acids or complex combinations of these substances, or may be living entities such as cells and tissues. Biologics are isolated from a variety of natural sources—human, animal, or microorganism—and may be produced by biotechnology methods and other technologies. Biologics include, for example and without limitation, monoclonal, polyclonal, humanized or chimeric antibodies, antibody fragments, or other binding reagents or ligands.

In certain aspects, the therapeutic agent is an anti-inflammatory agent, such as, without limitation, an NSAID, such as salicylic acid, indomethacin, sodium indomethacin trihydrate, salicylamide, naproxen, colchicine, fenoprofen, sulindac, diflunisal, diclofenac, indoprofen, sodium salicylamide; an anti-inflammatory cytokine; an anti-inflammatory protein; a steroidal anti-inflammatory agent; or an anti-clotting agents, such as heparin. Other drugs that may promote wound healing and/or tissue regeneration may also be included.

In certain aspects, cells are added to the composition, e.g., during or prior to mixing of the negatively-charged and positively-charged polyelectrolytes. Non-limiting examples of useful cells include: stem cells, progenitor cells and differentiated cells; recombinant cells; muscle cells and precursors thereof, nerve cells and precursors thereof; mesenchymal progenitor or stem cells; bone cells or precursors thereof, such as osteoprogenitor cells, etc.

In another aspect, compositions supportive of cell growth are added to the composition described herein, e.g., during mixing of the negatively-charged and positively-charged polyelectrolytes. In one embodiment, carbon allotropes are added to the composition, such as, without limitation: a carbon nanotube, a fullerene, fullerite, amorphous carbon, graphite, graphene, or carbon black.

Example 1

Figure 2:
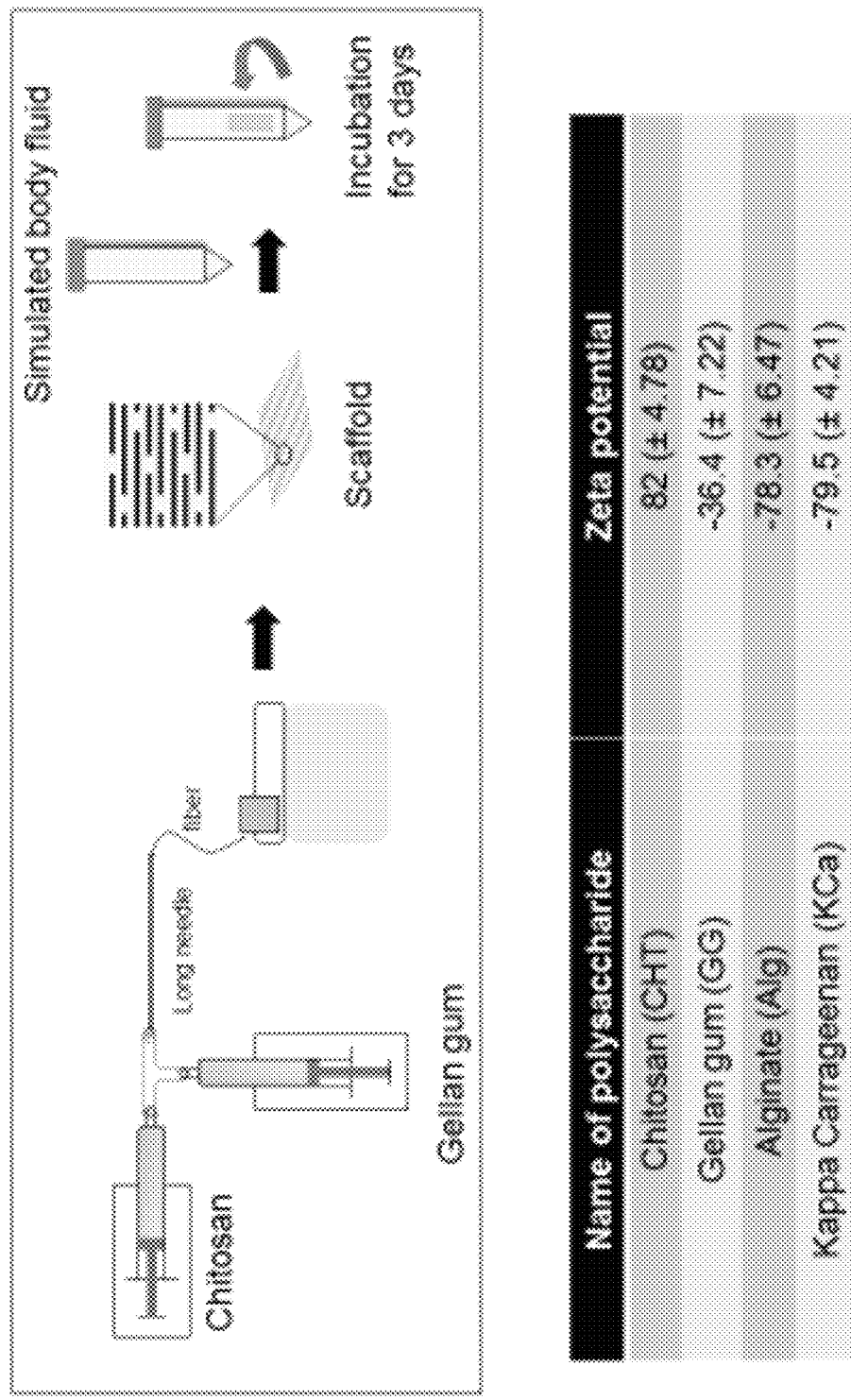
FIG. 2 shows a diagram of a method of preparation of scaffolds as described herein, and a table showing zeta potential of polysaccharide solutions.

In addition to charges, organic matrix in bone also possess parallel alignment at nanoscale which leads to hierarchy due to collagen self-assembly. Collagen fibrils and their bundles exhibit parallel alignment to each other in bone matrix. Fibrous structure of collagen creates well-organized arrays which provide a platform for precise crystal (mineral) orientation. Parallel alignment of fibers has proven to be crucial for parallel mineral deposition to achieve hierarchy at all length scales. To achieve parallel fiber alignment, method of fabrication was developed. In a non-limiting example of this method and a system for making the compositions described herein, as depicted in FIG. 2, 1% w/v solution of both positively and negatively charged polysaccharides came in contact with each other at a constant rate in microfluidic chamber to form fibers at the tip of 12 inch long 18 gauge stainless steel needle. These fibers were collected with the use of sharp pointed tweezers and arranged manually in parallel to each other to produce bilayer scaffold with 45 fiber in each layer. Such scaffolds were allowed to dry in air overnight. Once dried, scaffolds were easy to peel off from coverslip. Dried scaffolds can be easily handled with hands, allowing their folding to a considerable extent as well as cutting with scissors without disturbing overall structure of scaffold and orientation of fibers.

In additional embodiments, the needle can be replaced by microfluidic channel/chamber. Current optimized parameters are for making the process faster and more feasible for its production and not necessarily required, in principle, for making fiber fabrication possible. For example, fibers can be made at slower rate than current rate (50 mL/h), for example up to 30 ml/hr. But faster rates (>50 mL/h) were not seen to produce continuous fiber formation for the polyelectrolyte pairs reported here. For chosen polyelectrolyte pair, needle diameter/length or microfluidic channel/chamber diameter/length are optimized. For example an 18 g needle is, in essence, a tube having a lumen (inner) diameter of 0.838 mm. Thus, for fiber formation, a tube or microfluidic passage of e.g., from 0.1 mm to 2 mm, 0.5 to 1.5 mm, or 0.75 to 1.0 mm, and having any length, e.g., from 1 to 48 inches, or from 6 to 24 inches, may be employed to produce the composition described herein. Collection of fibers can be achieved by any method.

Figure 3:
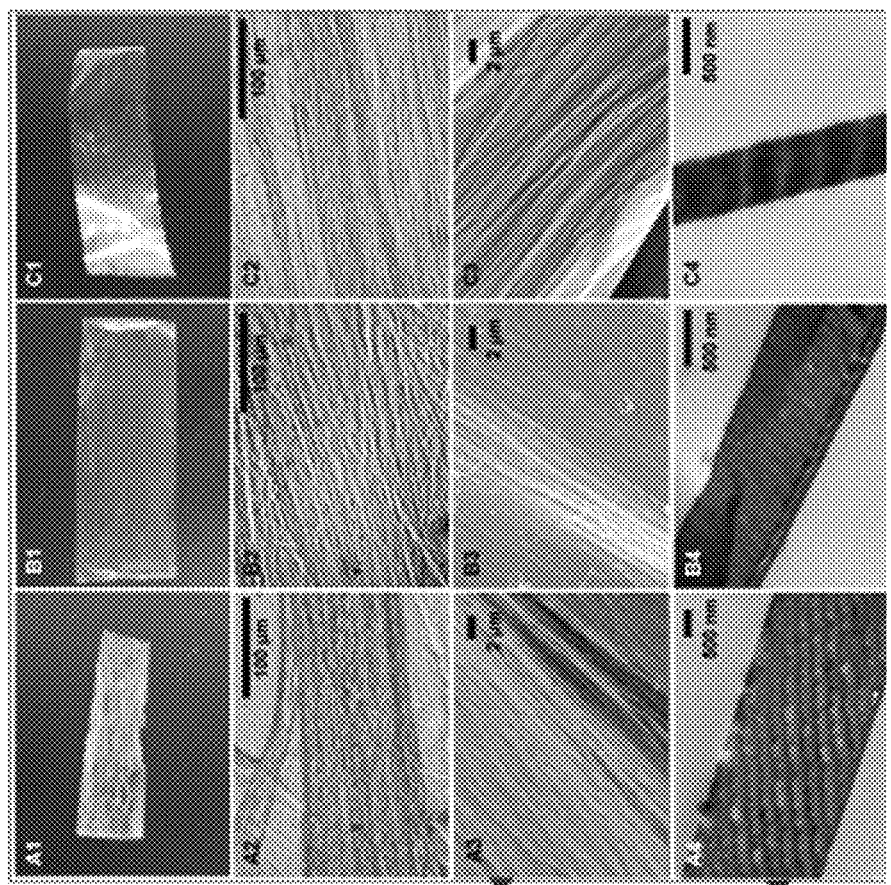
FIG. 3 shows fiber imaging at different scales.
Figure 3:
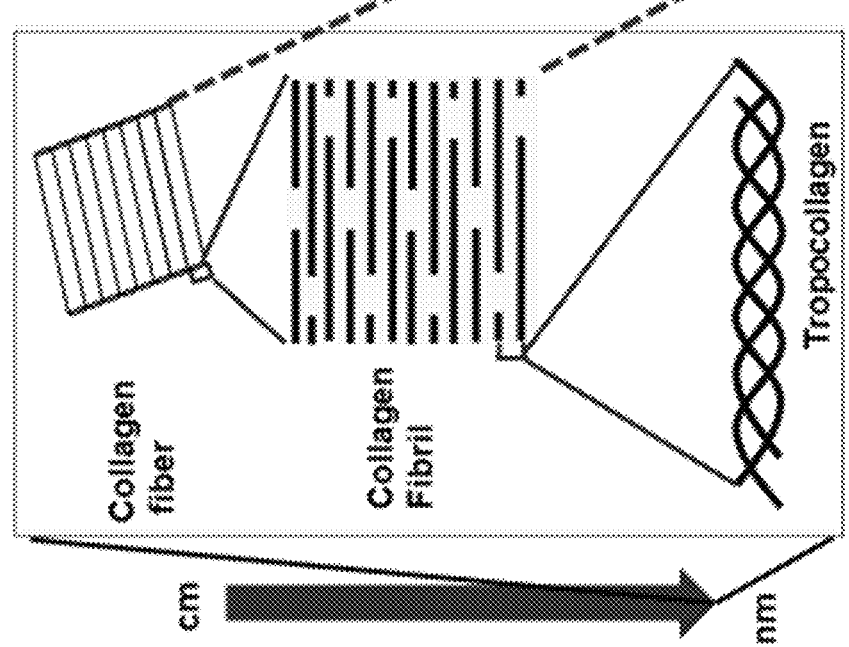

FIG. 3—(Visual picture, top row) shows dried scaffold at centimeter length scale. Light microscopy of freshly prepared scaffold reveals micro-scale fibrous structure and parallel alignment in scaffolds as seen in FIG. 3—(light microscopy, second row). Subsequent panel of scanning electron microscopy (SEM) images (FIG. 3—third row) reveals fibrous surface morphology which shows all three scaffolds with parallel fibrils within fibers. Collectively these three Figures show fibrous hierarchy at different length-scales. Transmission electron microscopy (TEM) reveals structure of fibers at nano-scale. As is evident from TEM images (FIG. 3—bottom row) for all three scaffolds show light and dark region forming bands as seen in collagen. We believe that it is the characteristic self-assembly between chitosan and three other selected polymers which results in light and dark regions within fibers. Thus, fabricated scaffolds have fibers made up of several fibrils which are believed to be self-assembled in the similar manner as tropocollagen self-assembly to result in dark and light bands.

Even with considerable progress in technology for nanoscale analysis, biomineralization studies continue to turn to in vitro experiments due to difficulty to investigate biomineralization process in vivo. Thus, widely used in vitro methods were employed to investigate biomineralization potential of proposed scaffolds.

In order to simulate ideal in vitro mineral sequestration, similar ion concentration to that of human plasma is required. To test potential of scaffolds to sequester minerals from solution simulated body fluid (SBF), which has same ion composition as plasma, was used. Table 1 provides composition of an exemplary SBF. Table 1 provides a formulation for 1×SBF, though 5× and 10×SBF can be used to promote mineralization.

TABLE 1

Order, amounts, weighing containers, purities and formula weights of reagants for preparing 1000 ml of SBF

| Order | Reagant | Amount | Container | Purity (%) | Formula weight |
|---|---|---|---|---|---|
| 1 | NaCl | 8.035 g | Weighing paper | 99.5 | 58.4430 |
| 2 | NaHCO$_3$ | 0.355 g | Weighing paper | 99.5 | 84.0068 |
| 3 | KCl | 0.225 g | Weighing bottle | 99.5 | 74.5515 |
| 4 | K$_2$HPO$_4$·3H$_2$O | 0.231 g | Weighing bottle | 99.0 | 228.2220 |
| 5 | MgCl$_2$·6H$_2$O | 0.311 g | Weighing bottle | 98.0 | 203.3034 |
| 6 | 1.0$_M$-HCl | 39 ml | Graduated cylinder | — | — |
| 7 | CaCl$_2$ | 0.292 g | Weighing bottle | 95.0 | 110.9848 |
| 8 | Na$_2$SO$_4$ | 0.072 g | Weighing bottle | 99.0 | 142.0428 |
| 9 | Tris | 6.118 g | Weighing paper | 99.0 | 121.1356 |
| 10 | 1.0$_M$-HCl | 0-5 ml | Syringe | — | — |

Dried scaffolds were hydrated in double distilled water for 3 hours prior to their incubation in SBF for three days at 37° C. and 100 rpm. As the definitive proof of concept, it was important to first look for potential of three different scaffolds to promote mineral sequestration from SBF. Fourier transform infrared (FTIR) spectroscopy is one way to confirm it. It characterizes the molecular environment of asymmetrically vibrating bonds in materials to detect different mineral content and mineral composition. After incubation of scaffolds in SBF for three days, scaffolds were flash frozen using liquid nitrogen and they were immediately subjected for overnight lyophilization. Same scaffold immersed in water under same condition for three days was chosen as control which was not expected to promote any mineral deposition. Lyophilized scaffolds were analyzed for changes in chemical composition with main focus on phosphate group peaks using Fourier transform infrared (FTIR) spectroscopy. KBr pellet method was employed to record the spectra as low as 500 cm-1.

FIG. 4 shows FTIR spectra for three scaffolds after incubation in SBF and water for three days. FIG. 4A compares FTIR spectra of CHT-GG scaffolds incubated in water and SBF. Scaffold incubated SBF shows peak at 597.9 cm-1 extending as a smooth curve with a tiny shoulder at 617.19 cm-1. Relatively smooth peak at 588.26 cm-1 in FIG. 4B indicates mineral deposits in CHT-Alg scaffold incubated in SBF. FIG. 4C shows mineral deposit found in CHT-KCa scaffold which has sharp peak with sharp shoulders at 597.9 cm-1 and 626.83 cm-1. All three mineralized scaffolds show a sharp peak at 1039 cm-1. Additionally, CHT-GG, CHT-Alg and CHT-KCa show 1053 cm-1, 1047 cm-1 and 1070 cm-1 shoulders respectively in sharp peak at 1039 cm-1. Smooth peak near 574 cm-1 indicates amorphous calcium phosphate (ACP) and sharp double peaks approximately at 540 cm-1 and 600 cm-1 indicate v4 vibration of phosphate group which is typical for hydroxyapatite (HA). 560 cm-1 peak instead of 540 cm-1 has also been reported to be confirming HA. Moreover, peak at 630 cm-1 suggests librational mode of OH— ions in HA (See Borodajenko, L.B.-C.a.N., Research of Calcium Phosphates Using Fourier Transform Infrared Spectroscopy, in Infrared Spectroscopy—Materials Science, Engineering and Technology, T. Theophanides, Editor. 2012, InTech). Peaks at 1072-1032 cm-1 are indicative of vibrations of phosphate group which can be found in all three mineralized scaffolds (See Koutsopoulos, S., Synthesis and characterization of hydroxyapatite crystals: a review study on the analytical methods. J Biomed Mater Res, 2002. 62(4): p. 600-12). Spectra for mineralized CHT-GG and CHT-KCa exhibit peaks resembling apatite whereas peaks in CHT-Alg indicate ACP like amorphous mineral depositions. However, few of these indicative peaks were observed as shifted from its precise confirmatory region, most of them have been detected exactly at indicative regions. In addition to phosphate, peaks indicating carbonated apatite (CAP) (1450-1465 cm-1) were also detected in mineralized scaffolds, indicating carbonated apatite depositions. As shown in FIGS. 4A, 4B and 4C, it is evident that all three scaffolds succeeded to sequester minerals from SBF, however, differing in the mineral composition.

Figure 4A:
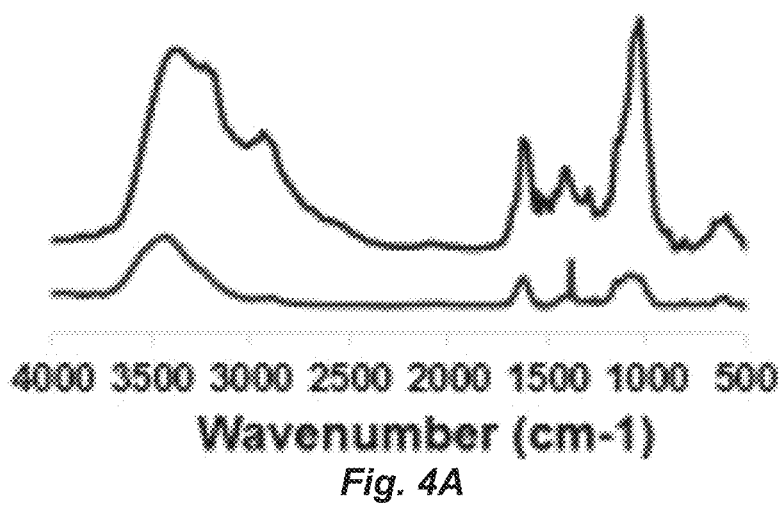
FIGS. 4A-4E.
Figure 4B:
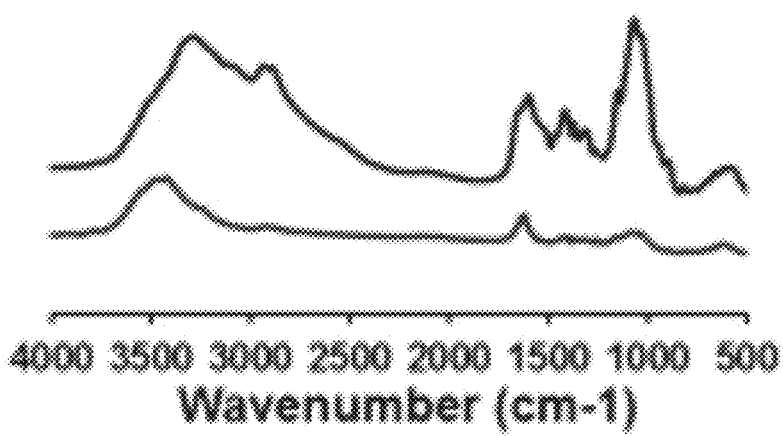
Figure 4C:
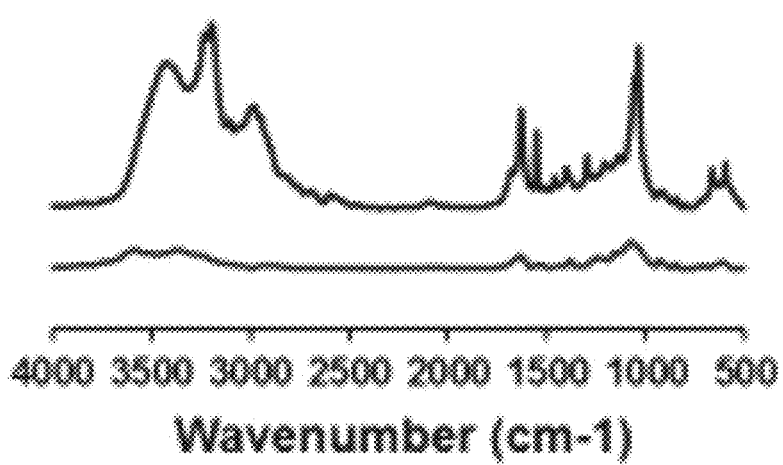
Figure 4D:
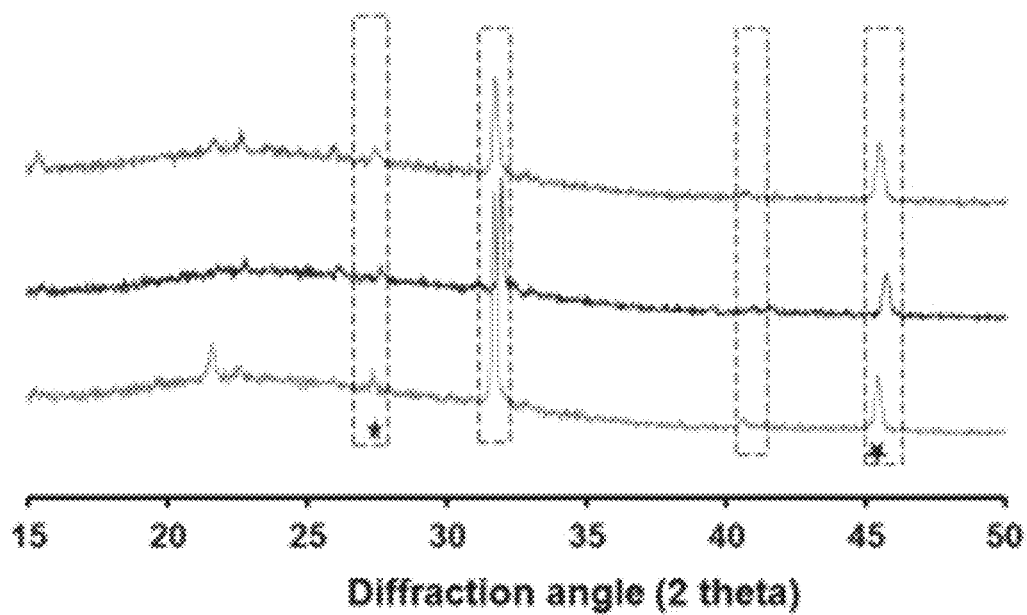
Figure 4E:
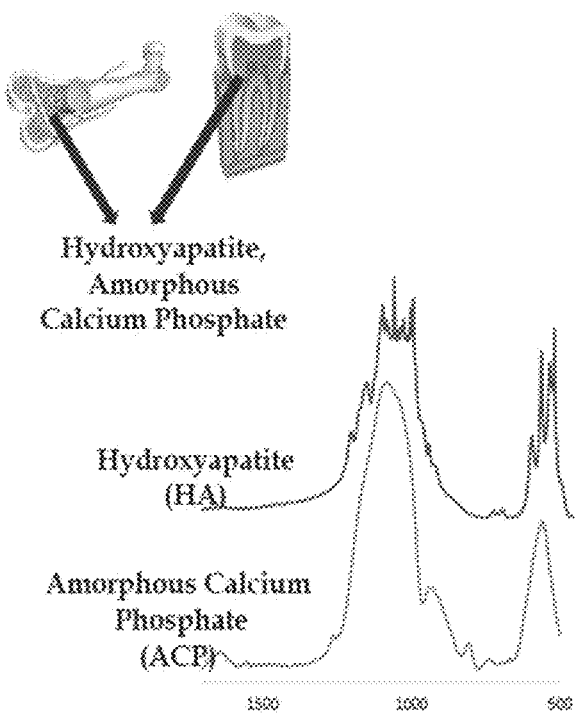

For definite proof of identity. X-ray diffraction (XRD) was employed. After three days of incubation in SBF, scaffolds were air dried and later crushed using mortar and pestle in order to ensure analyzing crystals of all different orientation. Samples were tested in Bruker D8 Discover XRD analyzer at generator voltage of 40 kV and current of 40 mA. FIG. 4D shows XRD spectra of three scaffolds in which stars on X-axis indicate the standard XRD pattern of HA (00-001-1008) (See Pishbin, F., et al., Electrophoretic deposition of gentamicin-loaded bioactive glass/chitosan composite coatings for orthopaedic implants. ACS Appl Mater Interfaces, 2014. 6(11): p. 8796-806; and Lala, S., et al., Biocompatible nanocrystalline natural bonelike carbonated hydroxyapatite synthesized by mechanical alloying in a record minimum time. Mater Sci Eng C Mater Biol Appl. 2014. 42: p. 647-56). XRD analysis of mineralized scaffolds confirm crystalline nature of collected mineral deposits as well as similar peaks to that of hydroxyapatite. Apatite like crystal deposits are seen for CHT-GG, CHT-KCa and amorphous deposits are seen for CHT-Alg. XRD spectra point to apatite-like crystal deposits for all three scaffolds.

Collectively, FTIR and XRD analyses support the capability of all three scaffolds to sequester minerals from SBF. Additionally, mineral deposits promoted by these scaffolds in vitro show crystalline nature except for FTIR spectrum of mineralized CHT-ALG scaffold.

Figure 5A:
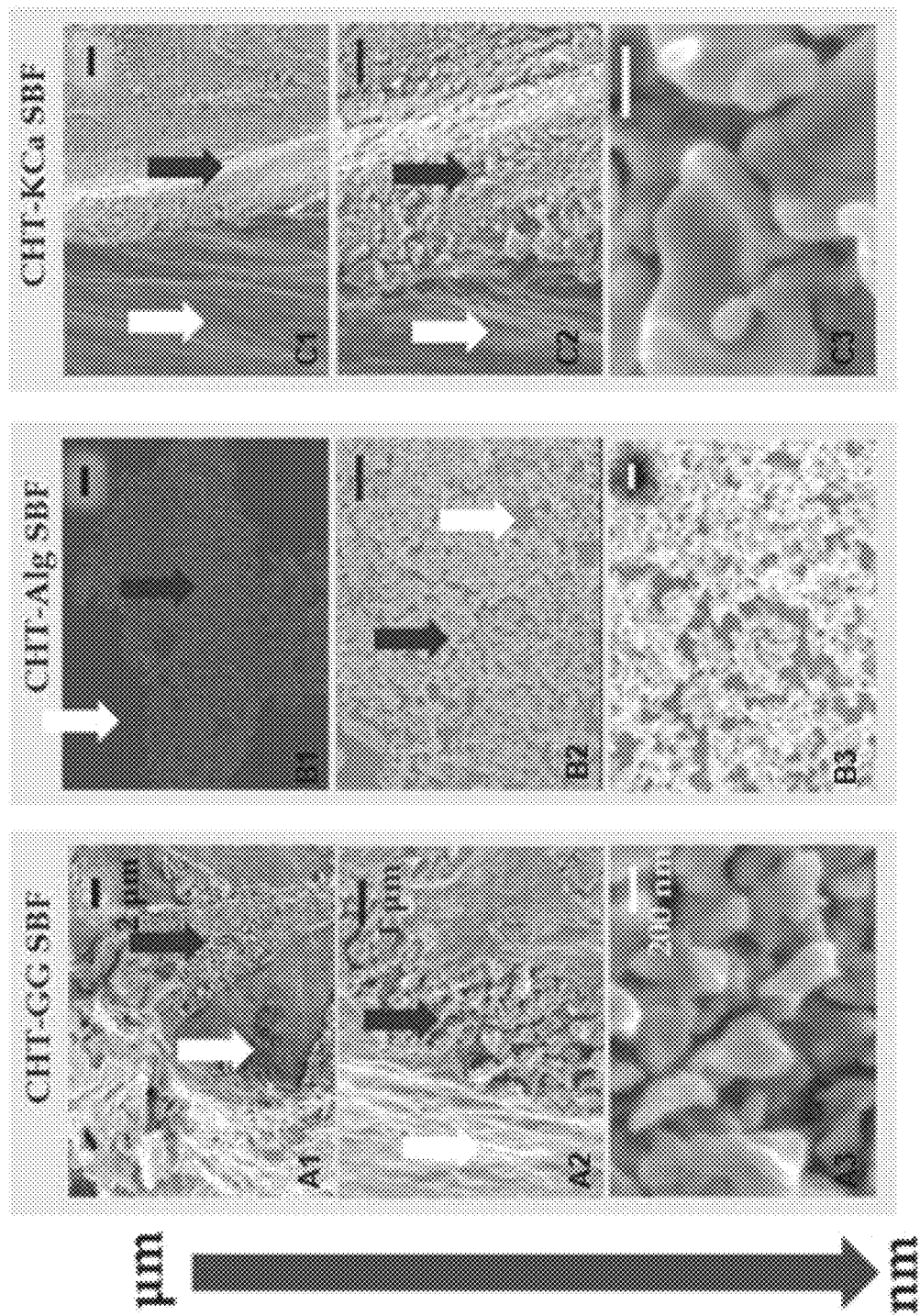
FIGS. 5A and 5B show scanning electron microscopy (5A) and transmission electron microscopy (5B) of mineralized hydrogel scaffolds.

Further, to investigate morphological features of deposited minerals on surface of scaffolds, scanning electron microscopy (SEM) was carried out. At lower resolution scale (FIG. 5—Top row), SEM images show localization of mineral deposition. It was interesting to observe aligned mineral deposition on CHT-GG and CHT-KCa scaffolds. CHT-ALG scaffolds were found to be promoting irregularly shaped clusters of mineral deposits. Higher magnification images reveal scaffold surface alteration due to mineral deposition as can be seen in FIG. 5—middle row. Mineral deposits on CHT-GG scaffold suggest their penetration into the scaffold surface. At same magnification scale, CHT-Alg shows minimal scaffold surface interaction of cluster of mineral deposit whereas CHT-KCa shows similar surface interaction to CHT-GG except no clear evidence for surface penetration. Very high magnification can provide information about mineral morphology as can be seen in FIG. 5—bottom row. Minerals on surface of CHT-GG and CHT-KCa scaffolds seem to be coarser than that of CHT-Alg scaffolds. Boskey concluded that biomineral deposits on surface not only guide ultimate crystal orientation within fibrils but they also dictate their size and shape. Moreover, the finding that anionic macromolecular matrix acts as a regulator of mineral deposition reiterates role of anionic polyelectrolytes similar to collagen. It can be observed that both carboxylate and sulfate functional groups show great extent of apatite formation on the surface of scaffolds, however, the difference in self-assembly between CHT-GG and CHT-Alg (both with carboxylate functional group) showed significant difference in the extent of apatite formation on the surface.

Figure 6A:
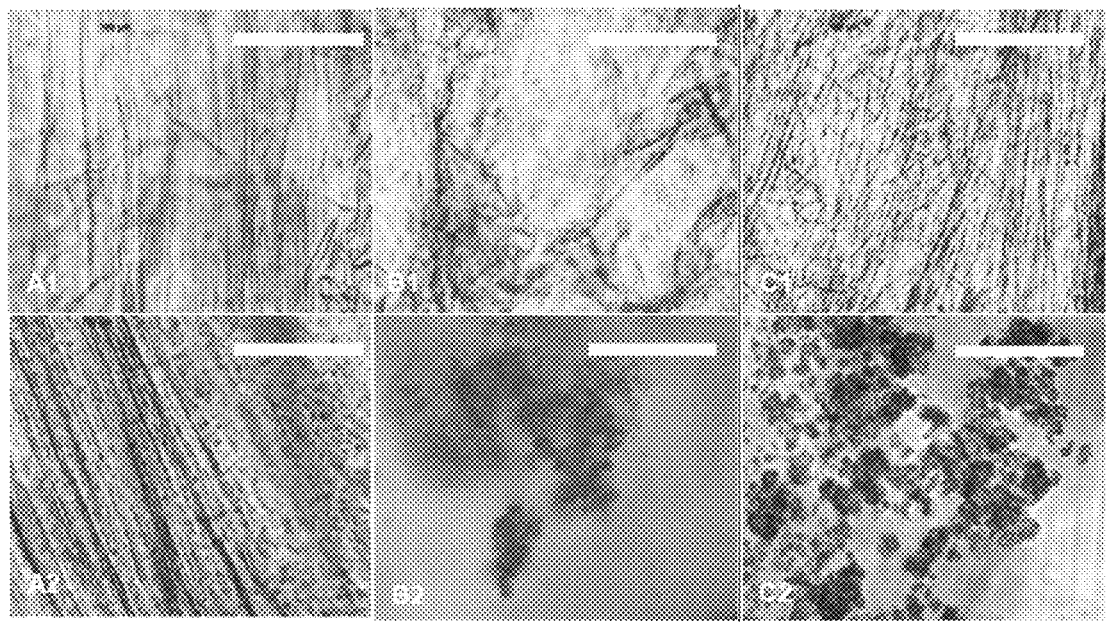
FIGS. 6A-6C show alizarin red staining of compositions as indicated (6A); a graph providing CPC Absorbance values (6B); provide SEM images after von kossa staining for phosphate (6C).
Figure 6B:
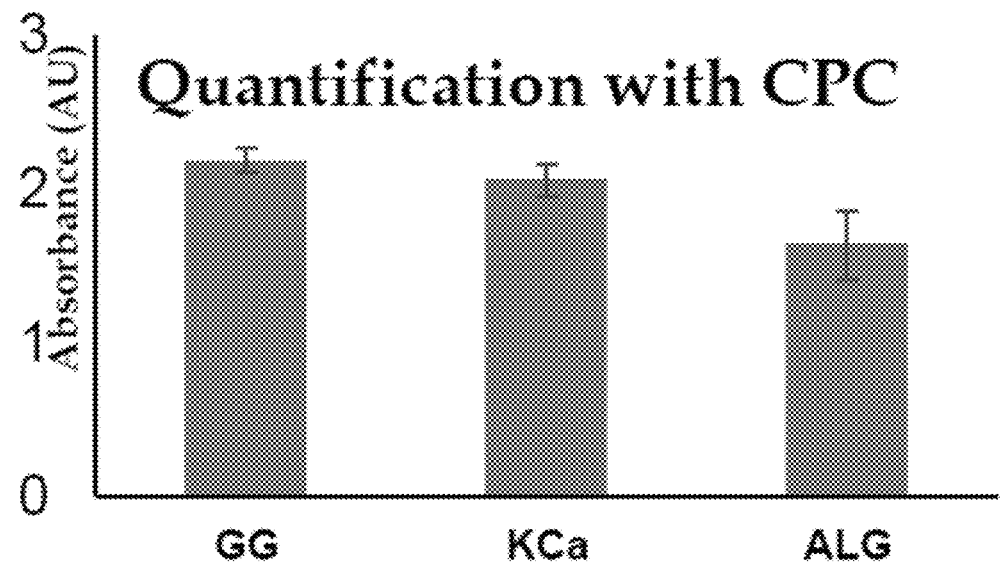

Calcium was identified by Alizarin red staining (FIG. 6A) and cetylpyridinium chloride was used for quantification (FIG. 6B). Staining and imaging: 40 mM of Alizarin red S (S25131 Fisher science) solution was prepared in water. 2 mL of freshly prepared solution was added to scaffolds in a petri plate for 30 seconds for 0.25 mm2 scaffolds. Light microscopy pictures were acquired.

Quantification of alizarin red: 10% w/v cetylpyridinium chloride (CPC, C0732) was prepared in distilled water. For a 0.25 mm2 scaffold, 5 mL of 10% w/v CPC was added and it was incubated in a shaker incubator overnight at 37° C. and 100 RPM. Absorbance was read at 570 nm in UV spectrophotometer.

Figure 6C:
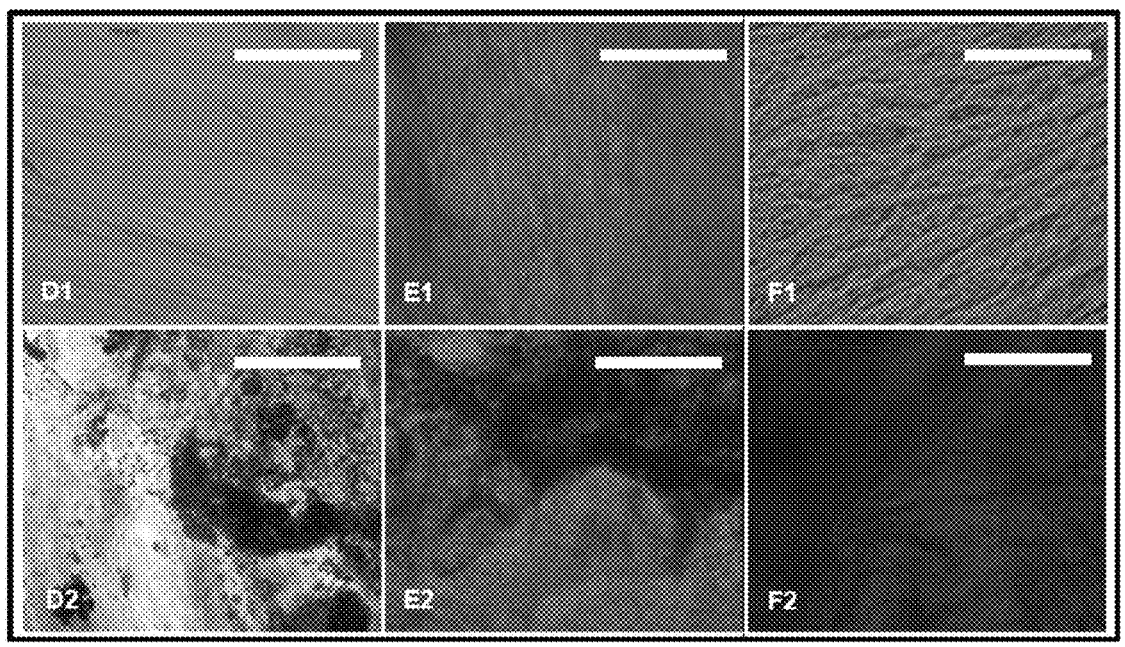

Phosphate was identified by Von Kossa Staining, as shown in FIG. 6C. Von Kossa staining: Mineralized or non-mineralized scaffolds were immersed in 2 mL 5% w/v silver nitrate (AgNO3, ACROS organics 419360250) solution under UV light for 5 minutes. After aspirating the solution and washes with distilled water from, 0.5% hypo (sodium thiosulphate) (Fisher chemicals M-10689) was added for 5 minutes. Excess hypo solution was removed and scaffolds were imaged using light microscopy. SEM images reveal larger mineral deposits in CHT-GG and CHT-KCa that those of CHT-Alg. Calcium and phosphate containing mineral are confirmed to be present with alizarin red and von kossa staining.

Figure 7A:
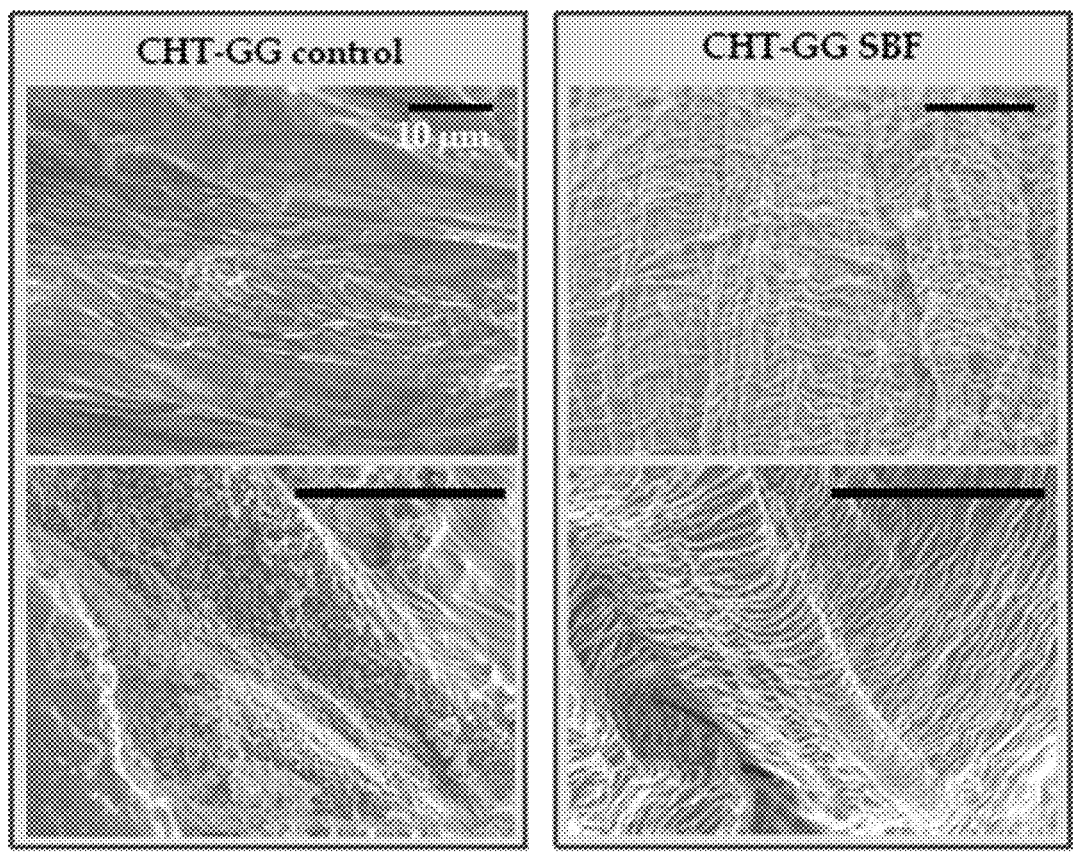
FIGS. 7A-7B provide SEM image of non-mineralized (left) and mineralized (right) CHT-GG (7A) and quantitative data on UTS of non-mineralized and mineralized scaffolds (7B).
Figure 7B:
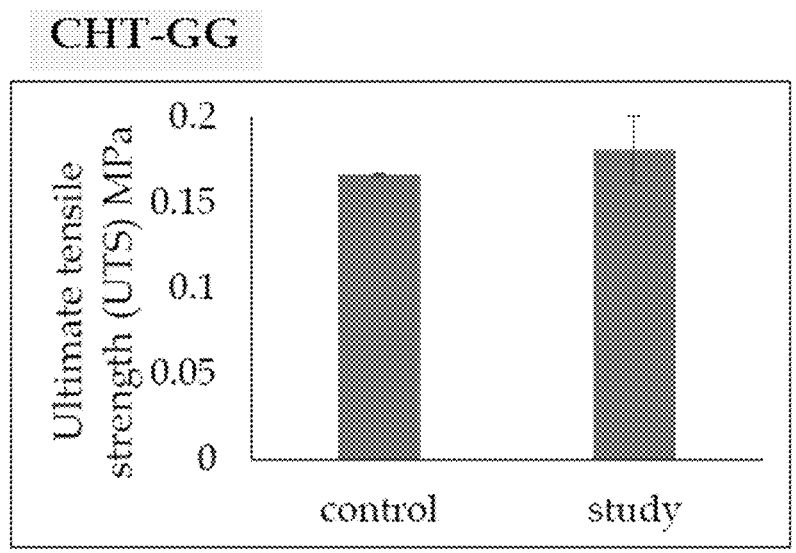

Effect of mineralization on mechanical properties: Immediately at the end of three days incubation, CHT-CG scaffolds of respective condition (control with no SBF and "SBF", incubated three days with SBF) were fixed in paper window using super glue. Great care was taken so as not to allow even a small amount of glue to touch the scaffold region to be tested. These scaffold windows were then tested using Texture Analyzer (TA-XT plus) for tensile strength and the calculation for interpretation was carried out considering the width and thickness of scaffold as its cross section. Images are shown in FIG. 7A, and tensile strength is shown in FIG. 7B. Mineralized scaffolds show resistance to their deformation in comparison to non-mineralized one. Ultimate Tensile Strength increases, however, not significantly in 3 days.

Although the mechanisms of mineralization are not fully understood, mineral sequestration, nucleation and its growth have been found to constitute three key steps in the process. Many mechanisms have been postulated in past to describe mineralization, of which, the one with considerable amount of consensus describes both intracellular and extracellular mineral deposition promoted by anionic extracellular matrix. The organic extracellular matrix work as a template and sequesters minerals/ions. It also promotes nucleation or a diffusion based process. Intrafibrillar and interfibrillar collagen mineralization are widely debated topics, however, the importance of collagen in the mineralization process is undisputed.

Further, to investigate potential of three scaffolds to sequester minerals inside scaffold material as well as to investigate their ability for promoting intrafibrillar and interfibrillar mineralization. TEM was employed. After three days of incubation in SBF, mineralized scaffolds were flash frozen and lyophilized. Dried scaffolds were embedded in Epon before sectioning. Sectioned samples were kept on grid to scope it in JEM-1011 electron microscope. Sections were not stained so as to exploit natural difference of electron density between mineral deposits and fibrous scaffolds for their TEM imaging. Mineral deposits being more electron dense, show greater electron transmittance leading to darker image while scoping. It is evident from FIG. 5B that all three scaffolds could successfully sequester minerals beyond scaffold surface. Interestingly, intrafibrillar mineral deposits were seen in CHT-GG (FIG. 5B D1) and CHT-KCa (FIG. 5B F1) scaffolds whereas in CHT-Alg scaffold (FIG. 6C E2), it was interfibrillar. Higher magnification image (FIG. 5B D2) of one of the section from CHT-GG scaffold shows orderly arrangement of nucleated mineral deposition, and very high magnification image (FIG. 5B D3) Shows precisely ordered and identically distanced mineral deposits. CHT-Alg scaffold show interfibrillar amorphous mineral deposits as well as it shows fine minerals at the periphery of fibers which seem to be mineral ions quenched from SBF. Collagen has a structural hierarchy with uniformly distanced staggered (hole-region) and eclipsed/overlapping regions which give it characteristic dark and light bands. At nanoscale, such structure exhibits periodicity in banding pattern (distanced at 64-70 nm) which is believed to be controlling mineral deposition. The mineral deposition follows structural and physicochemical influences exerted from the collagen structure and ends up forming periodic patterns of mineral deposition. Mineral deposition and growth may be facilitated by steric hindrance as an influence from neighboring hole region altogether with functional role of NCPs.

Figure 5B:
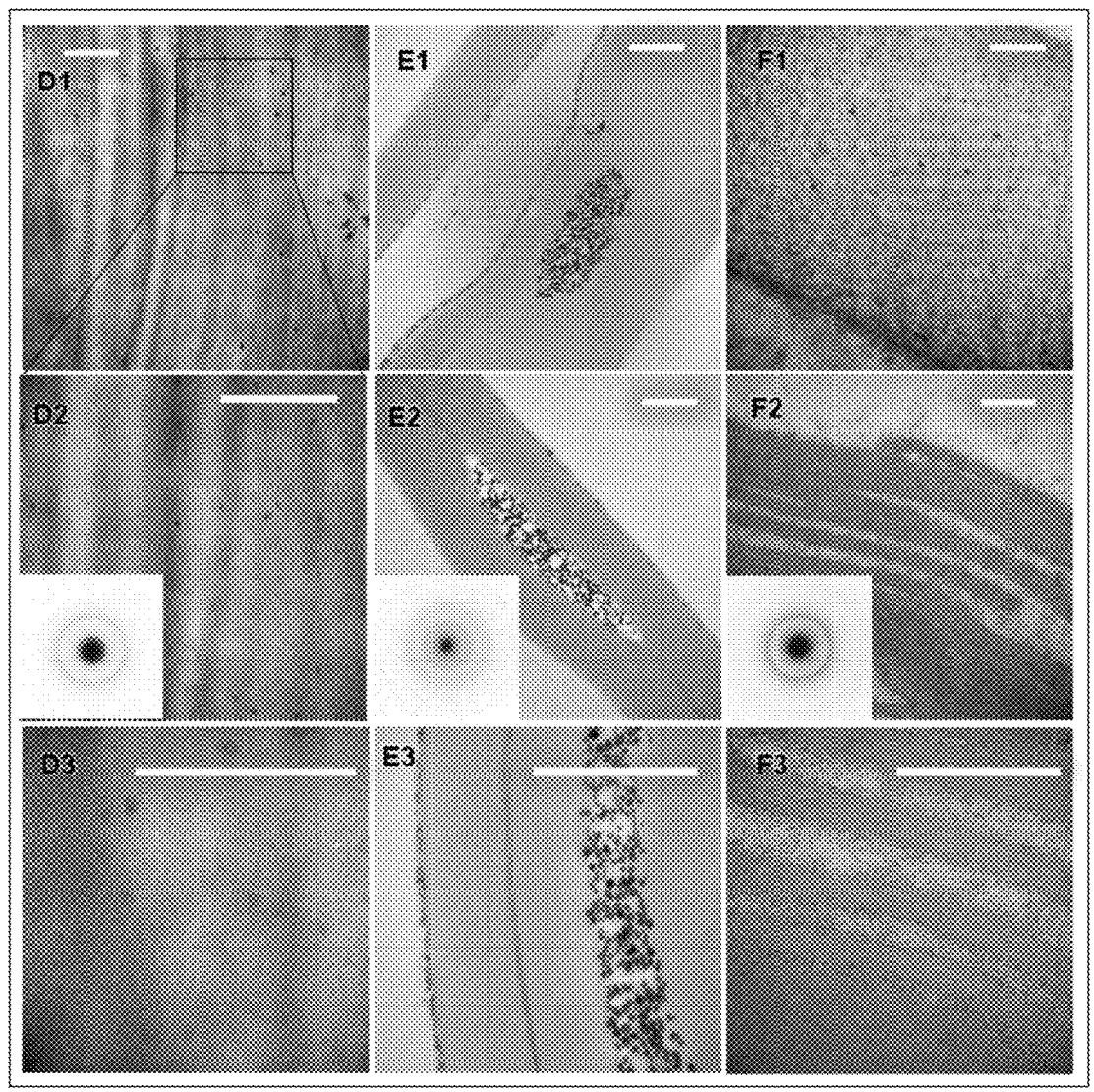

Confirmation of amorphous mineral deposits in CHT-Alg scaffold resonate with its evaluation by FTIR. However, mineral characterization of CHT-Alg using XRD revealed presence of apatite like mineral deposition as well which suggests possibility of separate nucleation and growth of apatite like minerals from fine crystal quenched on periphery of fibers to an extent which cannot be detected by FTIR. CHT-KCa scaffold show massive mineral ion sequestration from SBF in comparison with other two scaffolds. Interestingly, as can be seen in FIGS. 5B F1 and 5B F2, assembled or nucleated larger mineral deposits can be observed similar to that of CHT-GG and very fine quenched mineral ions are also visible.

FTIR revealed difference in mineral deposition for CHT-GG and CHT-Alg in which CHT-Alg showed phosphate peak similar to that of amorphous calcium phosphate. This result resonated with TEM image of CHT-Alg where interfibrillar amorphous deposits can be observed. CHT-KCa clearly showed apatite like phosphate peaks which resonated with its SEM image. CHT-GG and CHT-KCa scaffolds promote greater mineral deposition on surface compared to CHT-Alg which suggests effect of charge differences in polyelectrolytes being employed. Mineral deposition on surface is an important determinant for predicting potential of material in vivo (See Kokubo, T. and H. Takadama, How useful is SBF in predicting in vivo bone bioactivity? Biomaterials, 2006. 27(15): p. 2907-15). Moreover, for a material to be able to bind to bone in vivo, bone like apatite formation on surface is desired and this apatite formation can be simulated in SBF (See Kokubo, T., Bioactive glass ceramics: properties and applications. Biomaterials, 1991. 12(2): p. 155-63). Interestingly, trend observed in TEM monographs can be explained with SEM monographs. In CHT-GG and CHT-KCa scaffolds, SEM monographs reveal greater deposition mineral on the surface of scaffolds than CHT-Alg scaffolds, which prevents infiltration of diffusion of larger mineral deposits beyond surface in the former two scaffold types. Since CHT-Alg scaffolds don't deposit significant amount of minerals on the surface of scaffolds, more minerals are diffused inside the scaffold. As the sequestered minerals get saturated in CHT-Alg scaffolds, they can start aggregating intrafibrillarly as described earlier in FIG. 5B E1-E3. Diffusion kinetics of minerals into scaffolds depends on deposition of minerals on the surface. Comparison of CHT-GG and CHT-Alg scaffolds, which share carboxylate as charge imparting functional group, suggest role of amount of charge in sequestration of mineral pointing to its kinetics. Greater amount of negative charge (CHT-GG) with the same carboxylic acid functional group sequesters minerals faster on the surface than diffusion of minerals inside the scaffolds, allowing more time for them to aggregate on the surface of scaffolds. This deposition slows down the sequestration or diffusion of minerals into the scaffold mass. Whereas, comparison of CHT-GG and CHT-KCa, which have same amount of charge but carboxylate and sulfate as charge imparting functional group respectively, suggest dependence of mineral deposition on scaffold surface solely on amount of charge. However, as compared to CHT-Alg, these two pairs show less difference in morphology of mineral deposits on surface, pointing to collective role of charge imparting group and amount of charge.

Our bottom up approach incorporated self-assembly of natural polysaccharides in a manner similar to that of collagen. Three scaffolds show excellent ability to sequester and deposit ions from the simulated body fluid. Carboxylate and sulfate functional groups show similar extent of mineralization, however, they differ in chemical composition of deposited minerals. Size and location of mineral deposition inside the scaffold is proven to be dependent on speed of nucleation and growth of mineral deposits on the surface irrespective of functional groups. In addition to collagen-like property and hierarchy, our scaffolds also have charges as well as the functional groups similar to natural extracellular matrix. These scaffolds have potential for promoting natural biomineralization due to its biomimetic properties.

All three scaffolds promote in-vitro mineralization. Light microscopy, SEM, TEM confirmed aligned self-assembled fibrous scaffold structures, with fibrils within fibers and light and dark bands mimicking native collagen. FTIR and XRD studies confirmed the sequestration of minerals and their growth, to a limited extent, in scaffolds in 3 days in all three scaffolds, mostly amorphous in nature, showing partially crystalline structure in CHT-GG and CHT-KCa scaffolds. SEM of mineralized scaffolds shows variation in mineral morphology on surface and TEM shows differences in mineral deposition inside scaffolds as well, reiterating the hypothesis that differences in scaffolds are accountable for differences in mineral deposition observed. Alizarin red and Von Kossa staining confirms calcium and phosphate composite minerals. Quantification of Alizarin red yields no significant difference which suggest extent of mineralization to be almost same. SEM images of fractured CHT-GG scaffolds show mineralized scaffolds to be resistant to their deformation in comparison to non-mineralized ones.

Example 2—Biofunctionalization of the Hydrogel Fiber Bundle

Figure 8:
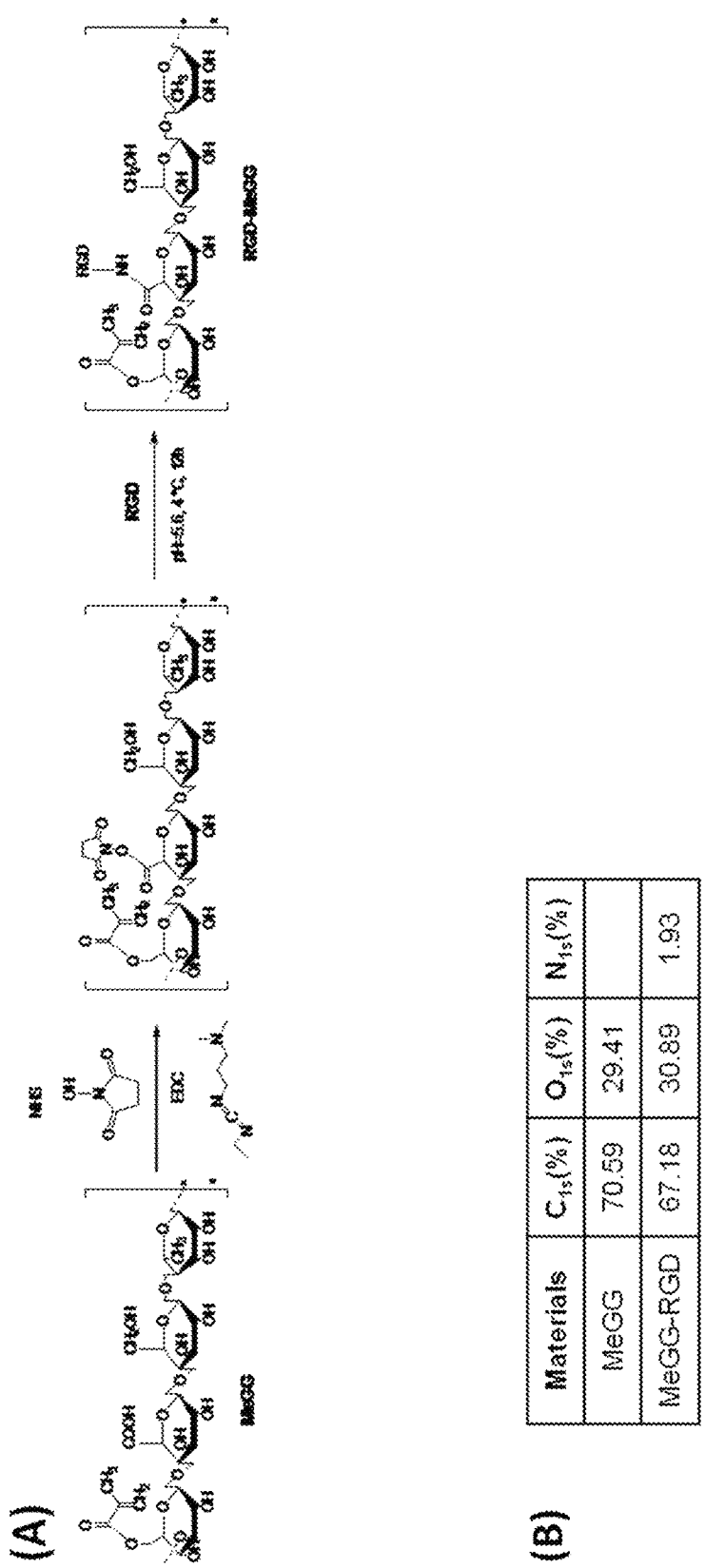
FIG. 8 show synthesis of RGD-MeGG. Panel (A) shows the chemical reaction. Panel (B) shows the elemental analysis of modified MeGG-RGD by XPS.

RGD sequence was covalently bound to gellan gum methacrylate (MeGG) using a water soluble carbodiimide. The procedure used for sequence immobilization was based on studies previously performed to immobilize amino-acid sequences on carboxylic-based substrates (See Lala, S., et al., Biocompatible nanocrystalline natural bonelike carbonated hydroxyapatite synthesized by mechanical alloying in a record minimum time. Mater Sci Eng C Mater Biol Appl, 2014. 42: p. 647-56). EDC reacts preferentially with the carboxyl groups of MeGG, activating them. Then, activated COOH of MeGG reacts with amine groups of the amino-acid sequence, covalently binding. Briefly, the pH of MeGG solution was stabilized at 5.6. 1-ethyl-3-(3-dimethylaminopropyl) carbodiimide hydrochloride (EDC, Thermo Scientific, 0.1 M) was added to 10 mL of MeGG and after 15 min, 0.2 M of N-Hydroxysuccinimide (NHS, Sigma) were added to the reaction. After 1 h of reaction, 200 µL of RGD (2.4 mg/mL) were added. The reaction continued for 12 hours under agitation, at 4° C. The solution was dialyzed for 2 days and kept at 4° C. after freeze drying. Two-dimensional hydrogels were fabricated by U exposure. FIG. 8 depicts synthesis of RGD-MeGG.

Figure 9:
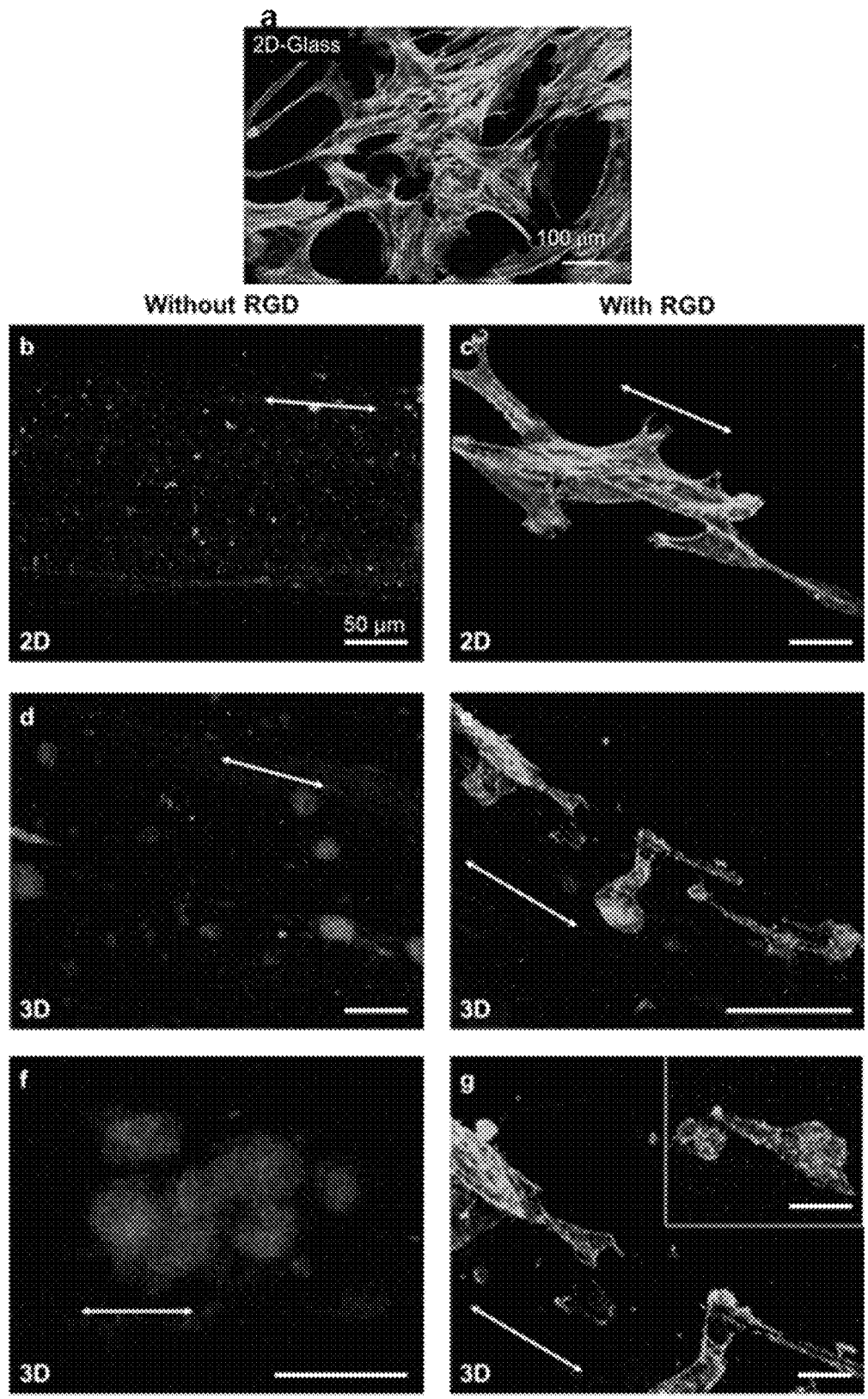
FIG. 9 shows biochemical mimicry of collagen-fibers. Panel A shows hMSCs seeded on 2D showed good spreading with no directional alignment. Preferential alignment of hMSCs along the axis of the MeGG-CHT fibers modified with RGD is seen both at 2D (Panel C) and 3D (Panels E and G) in contrast to a random distribution on the non-modified hydrogel fibers Panels B, D, and F). Scale bar, 50 µm. White arrows indicate direction of fiber alignment.

Example 3—Human Mesenchymal Stem Cell (hMSC) Culture on CHT-GG in 2D and 3D Culture FIG. 9: Biochemical mimicry of collagen-fibers. hMSCs (2×106 cells/mL) were seeded either on the fibers (2D) or encapsulated inside the fibers (3D). Fibers were fabricated using chitosan (CHT) and either plain gellan gum methacrylate (MeGG) or RGD-functionalized McGG to mimic integrin-binding sites in native collagen. hMSCs seeded in 2D glass was used as control.

Figure 10:
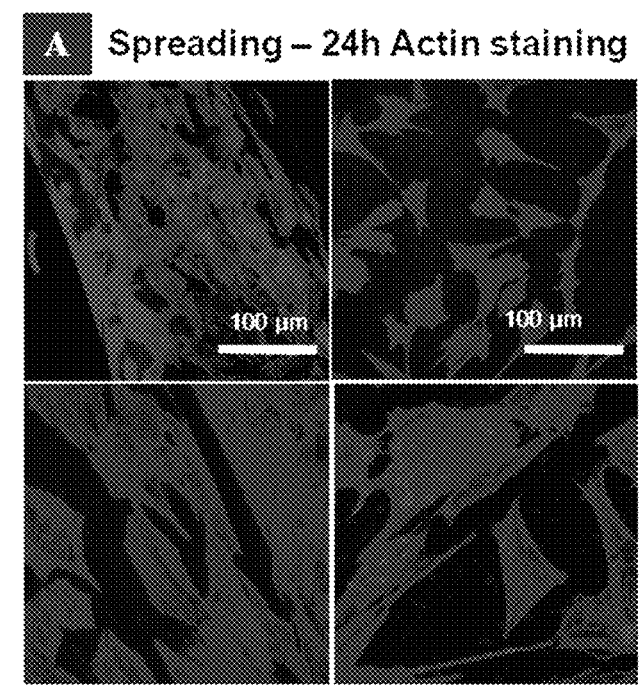
FIG. 10 shows data relating to graphene nano-functionalization of CHT-GG scaffolds for skeletal muscle tissue engineering. Panel A shows mouse myoblast cells (C2C12) seeded on CHT-GG for 24 hours in growth medium (DMEM+10% FBS); The top left and bottom left panels show actin (red in original) and DAPI (blue in original) staining after 24 hours of seeding and culture of C2C12 cells; The top right and bottom right panels show the same on CHT-GG with 0.01% Graphene in it. Panel B shows cell compatibility and proliferation assay; 14 days of culturing of cell seeded scaffolds in growth medium (alamar blue).
Figure 10:
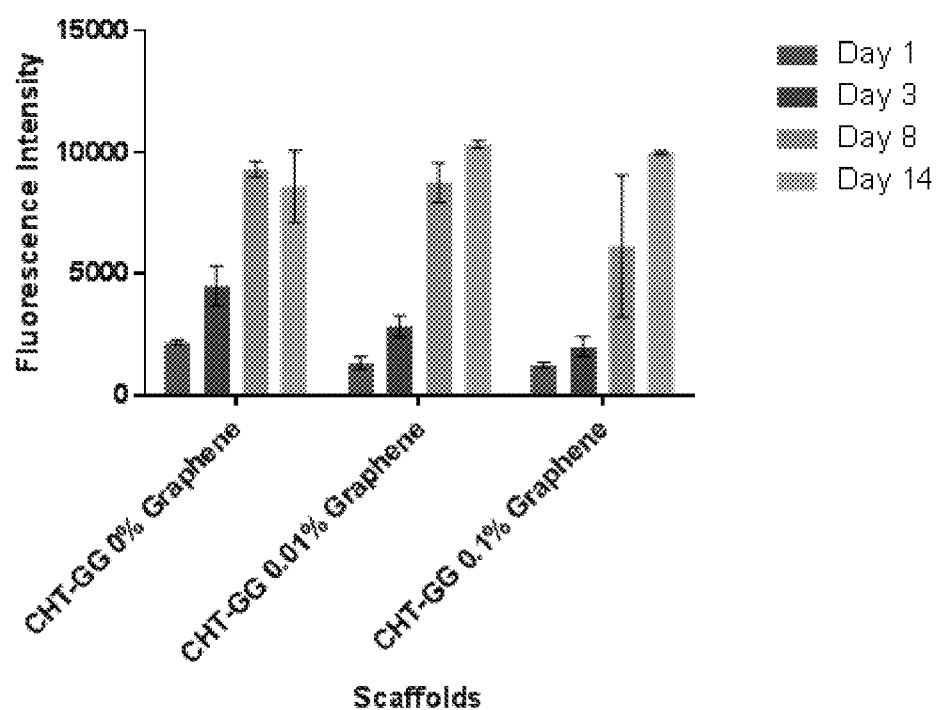

Example 4—Graphene Nano-Functionalization of CHT-GG Scaffolds for Skeletal Muscle Tissue Engineering FIG. 10: A: Mouse myoblast cells (C2C12) seeded on CHT-GG for 24 hours in growth medium (DMEM+10% FBS); top left and bottom left panels show actin (red in original) and DAPI (blue in original) staining after 24 hours of seeding and culture of C2C12 cells; The top right and bottom right panels show the same on CHT-GG with 0.01% Graphene in it. B: Cell compatibility and proliferation assay; 14 days of culturing of cell seeded scaffolds in growth medium (alamar blue)

These scaffolds can be modified with nano-scale substrates such as graphene or carbon nanotubes. Since they form composite based on electrostatic interaction, they are considered to be excellent materials for development of materials with undesired cell uptake masked by immobilization of these nano-scale substrates. Below is an example of CHT-GG graphene composite scaffolds in which prior to fabrication of the scaffolds 0.1% w/v graphene particles were suspended in 1% w/v chitosan solution in 1% v/v acetic acid.

Example 5—Drug Loading

Theoretically, all scaffolds described herein are capable of loading drug in them based on principle of electrostatic interaction based on charge. For example, CHT-ALG scaffolds were assessed for loading small molecules (model drug FITC) and protein/growth factor (model protein FITC-Bovine scrum albumin; FITC-BSA). FITC or FITC-BSA was dissolved in either of the two polyelectrolytes solutions prior to fabricating the scaffold.

Figure 11:
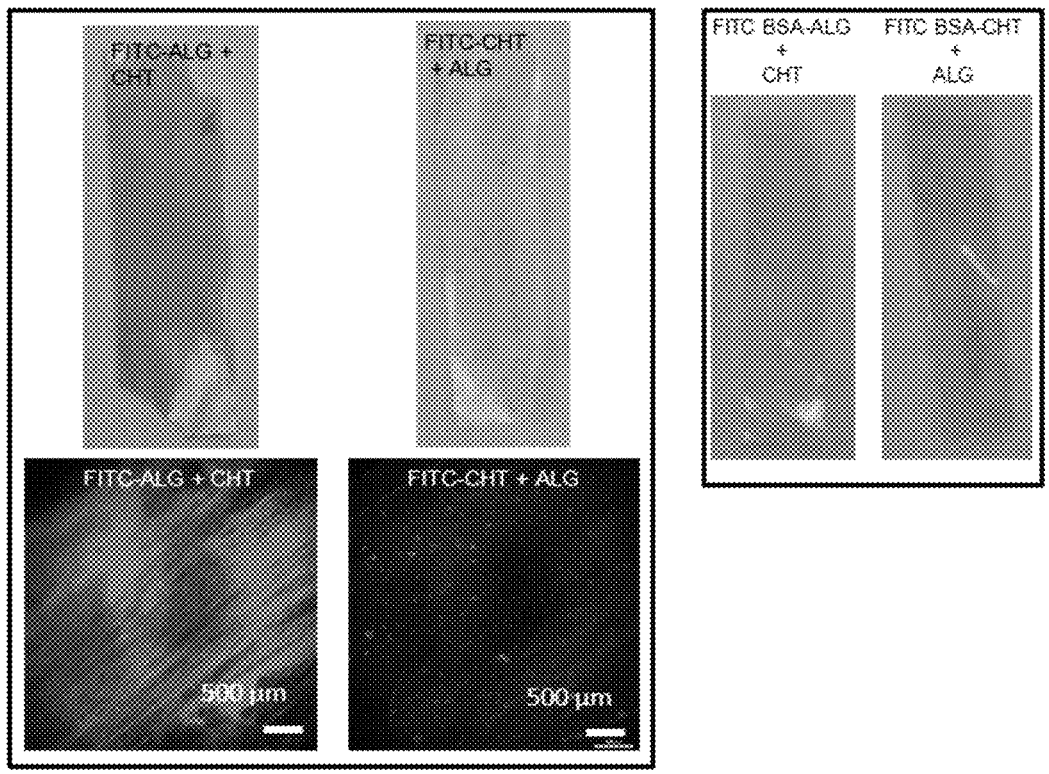
FIG. 11 shows photographs of FITC or FITC-BSA loaded CHT-ALG scaffolds; fluorescent images in lower panel shows more FITC loading when it was loaded in ALG solution prior to scaffold fabrication.
Figure 12:
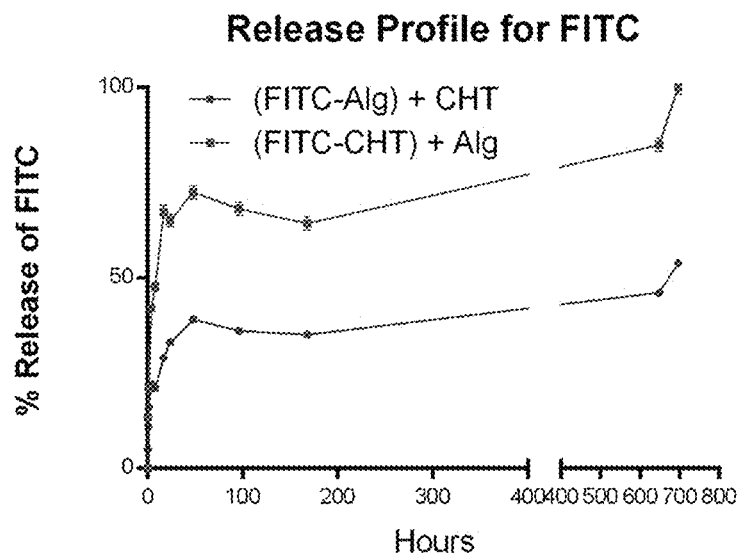
FIG. 12 shows the release profile for FITC in CHT-ALG scaffolds.

FIG. 11 provides photographs of FITC or FITC-BSA loaded CHT-ALG scaffolds; 5 mg FITC or FITC-BSA was loaded in either of the two polyelectrolytes; fluorescent images in lower panel shows more FITC loading when it was loaded in ALG solution prior to scaffold fabrication. FIG. 12 provides a release profile for FITC in CHT-ALG scaffolds; FITC-Alg indicates FITC dissolved in 1% w/v Alg solution in water prior to CHT-ALG scaffold fabrication and likewise FITC-CHT indicates dissolution of FITCC in 1% w/v CHT solution in 1% v/v acetic acid prior to the scaffold fabrication.

Example 6—Calvarial Model

Mice calvarial surgeries are performed in order to produce a repairable defect. Sheets of the positively- and negatively-charged polyelectrolyte are prepared essentially as above and are used to overlay the calvarial defect. Regenerated bone density and volume is determined using micro-computed tomography (µ-CT) at 0 days, 4 weeks and 8 weeks. Significant bone regeneration is expected, leading to complete regeneration with the same bone density as neighboring native bone at later time points. Histological analysis of the tissue is carried out at the end of week 8 to assess safety of the materials and the remodeling of bone following the implantation (efficacy).

Example 7—Biomimetic Self-Assembled Nano-Composite Hydrogel Promotes Myoblast Differentiation Introduction of two-dimensional conductive nanomaterials such as graphene has opened new opportunities in tissue engineering as it provides conductive interface for communication between electrically excitable myoblasts. However, it is challenging to achieve ECM-mimetic features conducive for myoblast differentiation by graphene alone. Meanwhile, hydrogels have shown great promise to incorporate various biophysical features such as optimum wettability, biomimetic soft three-dimensional structure to recreate regenerative microenvironment for myoblasts. However, they are limited due to their weak mechanical properties and/or use of toxic crosslinking agents. Provided herein is a cell-interactive interface, which can overcome individual shortcomings of graphene and hydrogels to fabricate a material with biomimetic biophysical factors. A fibrous hydrogel composite with multiscale structural hierarchy, aligned parallel fibers and a uniform array of graphene nanosheets was prepared by self-assembly of natural polysaccharides. Incorporation of graphene improved the mechanical strength of hydrogels. Toxicity due to graphene was overcome via the immobilization of graphene during self-assembly of hydrogel fibers. Graphene addition provided favorable wettability and nanoroughness for myoblast adhesion and spreading. These composites promoted differentiation of myoblasts into multinucleated dense myotubes. Overall, synergistic influence of fiber alignment, wettability and electric conductivity facilitated differentiation of myoblasts into multinucleated myotubes along the direction of fibers.

Carbon-based materials such as graphene and carbon nanotubes have surged in biomedical application recently. Among all carbon-based materials, graphene possesses unique properties such as high conductivity and charge carrier mobility, mostly due to its two-dimensional (2D) structure. For similar reasons, graphene offers superior promise for its potential for biomedical applications than other carbon-based materials. Extracellular matrix (ECM)-mimetic biomaterials are gaining importance as a central theme for most tissue engineering approaches. Extraordinary electrical properties and flexible processability of graphene make it an attractive candidate for achieving complex architectures. Specifically, skeletal muscle ECM possess several biophysical features such as conductivity for communication between myoblasts, multiscale hierarchical structure and fibrous alignment along with nanoroughness for contact guidance for the progenitor myoblasts, and strong yet elastic mechanical properties. In last few years, carbon-based materials such as carbon nanotubes and various forms of graphene have been explored for engineering regenerative skeletal muscle ECM. These approaches utilize unique electrical properties of graphene with or without external electrical stimulus. Although these materials hold great promise for restoring the cell-interactive ECM for the injured tissues, graphene-based tissue engineering approaches, by themselves, are limited in recreating the soft and flexible microenvironment conducive for myoblasts for their homing. Skeletal muscle tissue requires such microenvironment not just for the purpose of mechanotransduction but also for avoiding complications arising due to mechanical mismatch. It has proven challenging to fabricate graphene-based composites with such mechanical properties. Hydrogels are popular biomaterials for providing such microenvironment for initial cell homing; however, hydrogel use faces challenges in flexible processability for achieving a complex architecture. For example, use of hydrogels often requires the use of mostly toxic cross linkers to enhance its mechanical strength. While biophysical stimuli such as wettability and nanoroughness can be sensed by cells relatively earlier (almost immediately after coming in contact with the materials), other stimuli such as electrical conductivity and alignment are sensed later than the earlier homing of the myoblasts. For creating such a complex microenvironment in the material, a combination of biomimetic features of hydrogels and graphene is desired. Even though attempts have been made to design such composite materials, providing a useful product has proven challenging.

A cell-interactive interface is provided that combines the advantages and overcome the shortcomings of hydrogel and graphene resulting in a material with biomimetic biophysical factors. Chitosan (CHT) and gellan gum (GG) were combined along with graphene to form a composite hydrogel. The fibrous hydrogel composites have aligned parallel fibers with multiscale structural hierarchy and a uniform array of graphene nanosheets. Composite formation improved mechanical strength of hydrogels, keeping its elasticity intact. It also created favorable wettability for myoblast adhesion along with nanoroughness provided by graphene nanosheets, thus enhancing differentiation of myoblasts into multinucleated dense myotubes. The graphene composite scaffolds demonstrate great potential as a cell-interactive material for the differentiation of myoblasts.

Graphene (AO-2 nanopowder) was obtained from Graphene Supermarket (Calverton, N.Y., USA). Chitosan (C3646), gellan gum (G1910), and acetic acid were all purchased from Sigma-Aldrich, Co. (St. Louis, Mo., USA). Cell culture supplies, including Dulbecco's phosphate buffered saline (DPBS) and serum were purchased from Mediatech Inc. (Manassas, USA) or Corning Inc. (NY, USA) unless otherwise specified.

Particle size and zeta potential measurements for graphene-chitosan dispersion: Dispersion of 0.01% w/v, 0.05% w/v and 0.1% w/v was prepared in 1% w/v chitosan solution made in 1% v/v acetic acid. The particle size (hydrodynamic diameter) of graphene-chitosan (CHT) dispersion was measured by dynamic light scattering using a Malvern Zetasizer (Zetasizer 3000, Malvern, USA). Prior to measurement, graphene-CHT dispersions were freshly prepared and sonicated at 10% amplitude for 10 minutes using Fisher Scientific Sonic Dismembrator Model 500. The zeta potential of all dispersions, 1% w/v chitosan solution (0% graphene) and graphene dispersion in deionized water was also measured using the same instrument.

Transmission electron microscopy (TEM): Morphology of graphene and graphene-chitosan (CHT) dispersions were confirmed using transmission electron microscope JEOL 1011 (Joel, Tokyo, Japan) electron microscope operated at an accelerating voltage of 80 kV.

Fabrication of composite scaffolds: Graphene-CHT dispersion with different concentrations (0.01%, 0.05% and 0.1%) of graphene and 1% gellan gum solutions were allowed to self-assemble in a custom-designed chamber. Concentrations higher than 0.1% were not considered as fiber formation was not possible at these concentrations. Hydrogel fibers were collected to prepare a composite hydrogel scaffold. These scaffolds were allowed to air dry.

Measurement of contact angle: The wettability of composite scaffolds was determined by contact angle measurements. The contact angles of polymer films were measured using VCA 2000 video contact angle goniometer (AST products, n=at least 4). A droplet of de-ionized water was deposited on the sample film using a 21-gauge needle. The contact angles were determined by VCA software.

Electrochemical Characterization: Electrical impedance spectroscopy (EIS) was obtained from 1 Hz to 100,000 Hz in 1× phosphate buffered saline (PBS) with a Gamry Potentiostat, FAS2/Femtostat (Gamry Instruments) with Gamry Framework software. A three-electrode system with hydrated graphene composite scaffolds (4 hours in DPBS) as the working electrode, a platinum wire counter electrode, and a silver/silver chloride (Ag/AgCl) reference electrode was employed for the measurement.

Light microscopy: Light microscopy of dried scaffolds and C2C12 cell seeded scaffolds was performed using Zeiss Primo Vert microscope and images were acquired using Zen software.

Mechanical testing: The mechanical properties of hydrated composite hydrogel scaffolds were evaluated using uniaxial tensile testing with ADMET MTEST Quattro mechanical testing system (n=3). 2 cm×0.5 cm scaffolds were stretched until they break at a constant jogging rate of 10 mm/min. The stress (MPa) was obtained by dividing the applied force (N) with cross-section area (mm2) and % elongation (strain) was obtained by using ((L−L0)/L0)*100), in which L0 was considered as initial gauge length and L was considered as instantaneous gauge length. Ultimate tensile strength (UTS) was recorded as the maximum stress at sample failure. Similarly, toughness was calculated as the maximum energy (kJ/m3) required to break the sample. Young's modulus was calculated from the linear stress-strain curve between 5% and 15% strain. Toughness was calculated from stress-strain curves using OriginPro 6.

Scanning electron microscopy (SEM): Surface characterization of fractured scaffolds was carried out using SEM (JEOL 9335 Field Emission SEM (Xue Y. Patel A. Sant V. Sant S. PEGylated poly(ester amide) elastomers with tunable physico-chemical, mechanical and degradation properties. European Polymer Journal). Fractured scaffolds were air dried prior to SEM imaging. Dried samples were sputter-coated using 5 nm of gold-palladium using Cressington 108 auto sputter coater. Images were obtained using accelerated voltage of 3 kV and a working distance of 8 mm.

C2C12 mouse myoblast culture: The mouse myoblast cells (C2C12) cells were cultured in Dulbecco's modified Eagle's medium (DMEM) supplemented with 10% of heat inactivated Fetal Bovine Serum (HyClone™) and 1% antibiotic (Penicillin and streptomycin). The cells were cultured in T75 or T175 flasks in a humidified incubator at 37° C. and 5%° CO2. Fresh media was replaced with old media every 2 days and cells were split 1:3 at 70% confluence.

Cell seeding on scaffolds: Scaffolds with an area of 0.25 cm2 were sterilized for an hour in 100% ethanol under UV in a culture hood. The scaffolds were seeded with a seeding density of 90,000 cells/scaffold in 24-well plate. Each scaffold was transferred into a well after 1 day culture to remove non-adhered cells. Cells were cultured in growth medium for metabolic activity study and cells were cultured for 3 days in growth medium followed by additional 11 days in differentiation medium (DMEM supplemented with 10% horse serum HyClone™). Cells were seeded and cultured for 6 days for cell aggregate area study.

Metabolic activity of cells: The metabolic activity of cells seeded on scaffolds was measured using the AlamarBlue® assay (Thermo Scientific, USA) over 14 days. AlamarBlue® solution (10% v/v) was prepared in complete growth media and 500 µL of this solution was added to each well containing cell-seeded scaffold and incubated for 4 h at 37° C. After this step, 100 µL of the solution from each well was transferred to 96-well plate and the fluorescence intensity was measured at excitation/emission wavelength of 530/590 nm using the microplate reader (Synergy HT, BioTek instruments). The wells containing only AlamarBlue® solution in media were used as process controls for background fluorescence correction.

Immunofluorescence staining: Cell-seeded scaffolds were fixed using 4% paraformaldehyde for 20 min and washed 3 times with DPBS followed by the permeabilization with DPBS containing 0.1% Triton X-100 and blocking in DPBS containing 0.1% Triton X-100 and 5% BSA for 1 h at room temperature. The scaffolds were then incubated with the primary antibody against myosin heavy chain (MHC), MF-20 (1:50, DSHB, Iowa) overnight at 4° C. and washed with DPBS containing 0.1% Triton X-100 thrice. The scaffolds were then stained with secondary antibody (Alexa Fluor 488-conjugated rabbit anti-mouse IgG, 1:200 (A-11059) Molecular probest, USA) for 1 hour at room temperature followed by three times washing with DPBS. The cell nuclei were stained with Hoechst 33342 (Thermo Fisher, USA).

Confocal microscopy: Confocal images were obtained using inverted confocal laser scanning microscope (Olympus Fluoview 1000). Lasers of 488- and 633-nm wavelength were used. Objective lenses of 20× was used to acquire the z-stack images with 5 µm thickness of each z slice. Data is presented as maximum intensity projection of the z-stack.

Image analysis: NIH ImageJ software was used for quantification of light microscopy images. Images were first converted into 8 bit and then the threshold was set such that only aggregate areas show the contrasting color. After setting the contrast, ROI manager was used to pick the areas for measurement of aggregate areas. Ratio of total cell aggregate area to total area of the scaffold in each 4× image was taken.

Statistical analysis: The data are represented as mean±standard deviation (n is noted under each method and figure legends). The statistical significance between the groups was analyzed using one-way or two-way ANOVA and the multiple comparisons were carried out using Tukey post-hoc analysis (GraphPad Prism 6). p values less than 0.05 were considered statistically significant. p values are noted in the figure legends for the corresponding figures. All the bar graphs are plotted using GraphPad Prism 6.

Results

Characterization of graphene nanosheets and graphene-chitosan dispersion: Polysaccharides have been used in skeletal muscle tissue engineering, mostly by composite formation with other carbon-based materials such as graphene or carbon nanotubes (Goenka S, Sant V, Sant S. Graphene-based nanomaterials for drug delivery and tissue engineering. J Control Release 2014:173:75-88 and Ding X, Liu H, Fan Y. Graphene-Based Materials in Regenerative Medicine. Adv Healthc Mater 2015). Chitosan and gellan gum are two of the most widely explored polysaccharides for their application in tissue engineering (Coutinho D F, Sant S, Shakiba M, Wang B, Gomes M E, Neves N M, Reis R L, Khademhosseini A. Microfabricated photocrosslinkable polyelectrolyte-complex of chitosan and methacrylated gellan gum. J Mater Chem 2012; 22(33):17262-17271; Rabanel J-M, Bertrand N, Sant S, Louati S. Hildgen P. Polysaccharide hydrogels for the preparation of immunoisolated cell delivery systems. In: Marchessault R H, Ravenelle F, Zhu X X, editors. Polysaccharides for Drug Delivery and Pharmaceutical Applications: 2006. p 305-339; and Coutinho D F, Sant S V, Shin H, Oliveira J T, Gomes M E, Neves N M, Khademhosseini A. Reis R L. Modified Gellan Gum hydrogels with tunable physical and mechanical properties. Biomaterials 2010; 31(29):7494-7502). Both of them have shown great cytocompatibility for various applications.

Figure 13:
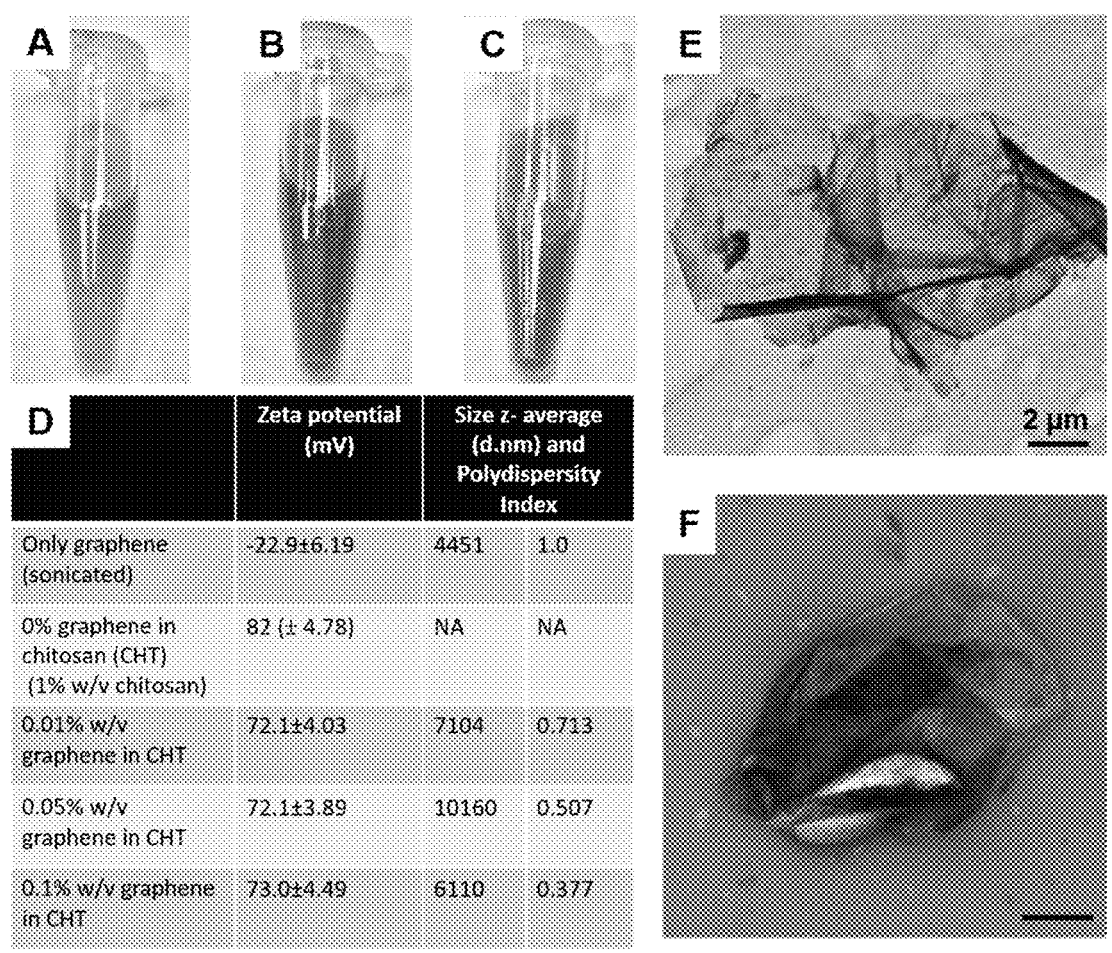
FIG. 13 shows the characterization of graphene nanosheets and graphene-chitosan dispersion. Panels A, B and C show photographic pictures of graphene-chitosan (CHT) dispersion of 0.01% w/v (A), 0.05% w/v (B) and 0.1% w/v (C) dispersion; Panel D shows tabulated values of zeta potential, size average and polydispersity index Panel E indicates transmission electron microscopy (TEM) image of graphene sheet, showing morphology of the graphene sheets in the original form, Panel F indicates TEM image of 0.05% w/v graphene in 1% w/v chitosan, similar images were obtained for all three concentrations of graphene in chitosan, however, as they showed the same morphology, only a representative micrograph of is shown here; scale bars represent 2 µm.
Figure 14:
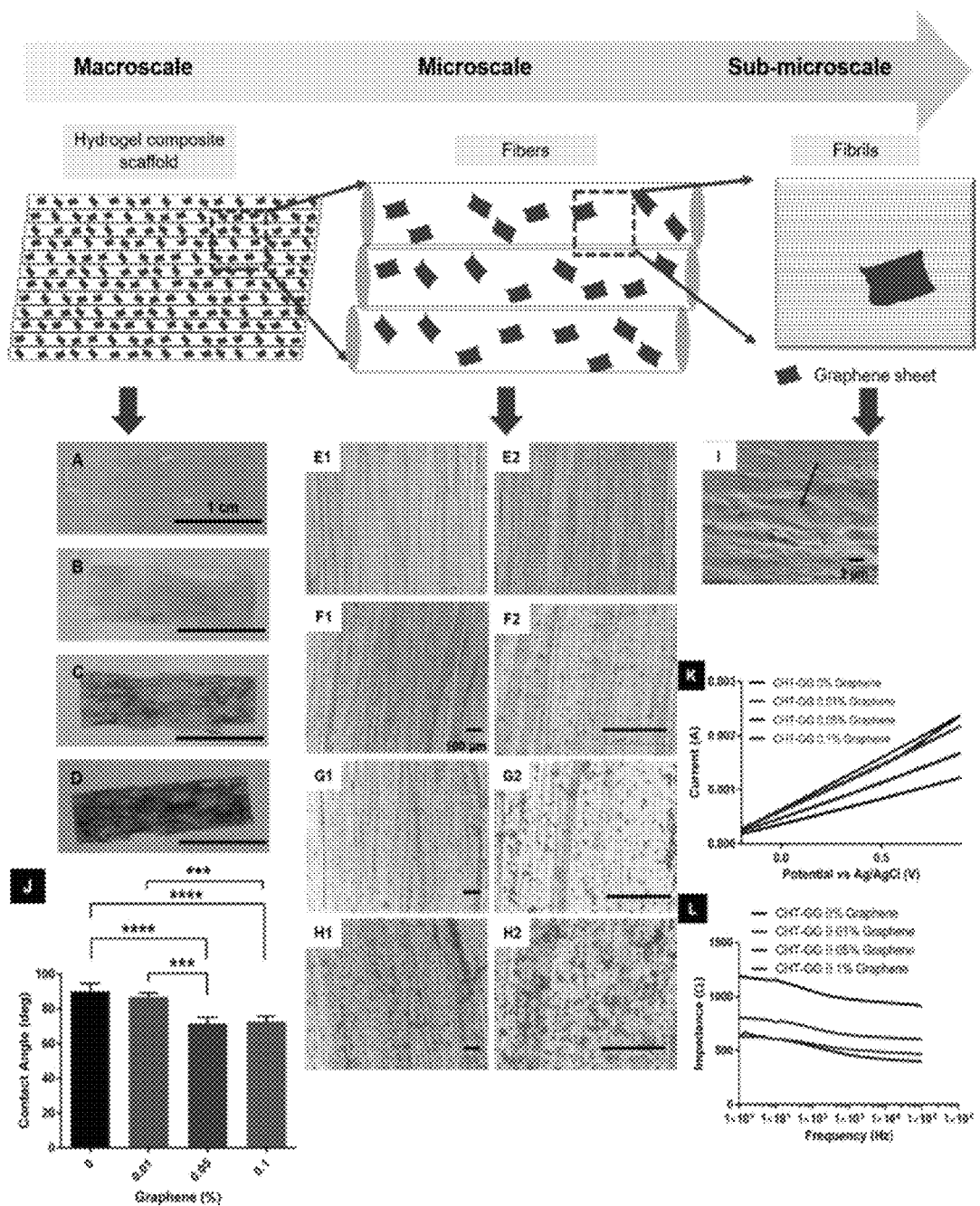
FIG. 14 show multiscale hierarchy and characterization of graphene-CHT-GG scaffolds. The schematic at the top of FIG. 14 shows the multiscale hierarchy of scaffolds spanning from macroscale composite scaffold structure to microscale fibers and sub-microscale fibrils; Panels A. B, C and D show photographic picture of CHT-GG 0% graphene control, CHT-GG 0.01% graphene, 0.05% graphene and 0.1% graphene, respectively, scale bars represent 1 cm; Panels E1 and E2 indicate 10× and 40× magnification light microscopy picture for CHT-GG 0% graphene (control) showing uniform distribution of graphene throughout the scaffold, Panels F1 and F2 indicate similar pictures for CHT-GG 0.01% graphene, Panels G1 and G2 indicate similar pictures for CHT-GG 0.05% graphene, Panels H1 and H2 indicate similar pictures for CHT-GG 0.1% graphene scale bars represent 100 µm; Panel I shows scanning electron microscopy (SEM) image of graphene sheet (indicated with red arrow) oriented in horizontal direction near the surface of scaffolds; Panel J represents contact angle measurements of different concentration of graphene composite scaffolds and control (CHT-GG 0% graphene) scaffolds (n=at least 4); Panel K shows a representative plot from cyclic voltammetry plot. It shows that all graphene composite hydrogels demonstrate higher current than the 0% graphene scaffolds; Panel L represents EIS from 1 Hz to 100,000 Hz. It shows lower impedance for all graphene composite scaffolds (solid lines) relative to 0% graphene scaffold (dashed line). Statistical significance was assessed by one-way ANOVA and Tukey post hoc test. * denotes $p<0.005$, ** denotes $p<0.0001$.

Concentrations of 0.01% w/v graphene-CHT, 0.05% w/v graphene-CHT and 0.1% graphene-CHT were prepared. All three concentrations resulted in stable suspension in CHT following sonication. Increasing concentration of graphene resulted in a slight increase in darkness of the solution as compared to the lower concentration graphene as shown in FIGS. 13 (A)-(D). Zeta potential and size analysis of graphene-CHT dispersion revealed charge neutralization due to the presence of CHT. Graphene suspension in distilled water with same sonication possessed negative charges and CHT alone possesses positive charge. As expected, Dispersion of CHT and graphene of different concentration resulted in neutralization of the positive charge by some extent. It decreased from 82 (±4.78) to 72-73 as shown in FIG. 13 (D). Average particle diameter increased for all three concentration of graphene-CHT dispersion as shown in FIG. 14 (D). Specifically, 0.01% and 0.05% graphene-CHT showed higher average particle diameters with higher polydispersity whereas 0.1% graphene-CHT showed smaller average particle diameter than the other two lower concentrations with lesser polydispersity. Moreover, polydispersity decreased as the concentration of graphene increased from 0.01% to 0.1%. Further, TEM of the graphene-CHT dispersion was performed to assess the morphological changes in graphene sheets due to the presence of CHT. All three concentration of graphene-CHT dispersion showed similar morphology of graphene. A representative image of 0.05% graphene-CHT is shown in FIG. 13(F) which doesn't have irregular edges as seen in FIG. 13 (E).

Reduced form of graphene oxide is also used for various advantages of functionalization over graphene, however, it decreases its conductivity significantly. For SMTE, conductivity is one of the important biophysical factors, therefore graphene was used in this study. Since the graphene nanosheets used in this study possessed negative charge (FIG. 13 (D)), it was decided to mix with 1% w/v solution of CHT. In order to improve uniformity of the graphene-CHT dispersion, it was homogenized. TEM micrographs revealed similar morphological of graphene nanosheets for all concentrations of graphene-CHT (FIG. 13 (E), (F)), indicating that the CHT did not affect the morphology of graphene except encapsulating graphene sheets.

Multiscale hierarchy and characterization of graphene-CHT-GG scaffolds: Researchers have reported highly interconnected and porous graphene aerogels and, other nanocomposites. However, the combination of various biophysical factors essential for the recreation of ECM mimetic microenvironment has been challenging. With the methods and materials described herein, complex biophysical features are successfully combined. Moreover, the self-assembly process obviated the need for toxic crosslinking agents, providing an edge over other hydrogel biomaterials for biocompatibility. The highest concentration considered for the composite formation was 0.1% w/v graphene. Higher concentrations than this disrupted the fiber formation due to change in electrostatic interaction in the microfluidic chamber (data not shown). Since the scaffolds were found to be mostly transparent (FIGS. 14 (A-D)), light microscopy was utilized to confirm the distribution of graphene sheets in the scaffolds as well as the multiscale hierarchy.

Self-assembly based fabrication method yielded reproducible fibrous scaffolds with a multiscale hierarchy as shown in the schematic in FIG. 14. These composite scaffolds are named on the basis of the concentration of graphene-CHT dispersion used during fabrication. Scaffolds made with 0.01% graphene-CHT and GG are described as CHT-GG 0.01% graphene scaffolds hereafter. Likewise, other types of composite scaffolds are described as 0.05% graphene and 0.1% graphene scaffolds. FIGS. 14 (A)-(C) show macroscopic appearance of the three types of dried composite scaffolds. Scaffolds were mostly transparent and assumed darker color as the concentration of graphene increased. Dried scaffolds were easy to handle and the hydrated scaffolds could be easily transformed into various shapes. Light microscopy images revealed uniform distribution of the graphene throughout the in 0.01% graphene scaffolds as well as linear alignment of the fibers in one direction. Similarly, uniform distribution of graphene and aligned hydrogel fibers were confirmed in 0.05% graphene (FIG. 14 (G1) and (G2)) and 0.1% graphene scaffolds (FIG. 14 (H1) and (H2)). FIG. 14(I) represents a graphene sheet on the surface of the scaffold. Such graphene sheets may enhance the surface nano-roughness of the composite scaffolds, leading to a change in contact angle as well as cell adhesion and spreading. Scaffolds demonstrated similar to the multi-scale hierarchy of the skeletal muscle (FIG. 14 (E1)-(H2)), which spans from myofibrils at microscale to muscle bundle at macro scale. This may provide geographical guidance for the myotubes during the developmental process into functional muscle bundle.

Further, surface wettability was characterized by the measurement of contact angle using water droplet. Interestingly, graphene composite formation significantly changed the contact angle compared to the 0% graphene scaffolds (FIG. 14 (J)). Moreover, the contact angle reduced among composite scaffolds as the concentration of graphene was increased from 0.01% to 0.05%. However, further increase in graphene concentration from 0.05% to 0.1% in the composite scaffolds didn't significantly change contact angles. The reduction in contact angel indicates an increase in the wettability of the surface. Wettability of the surface plays an important role in modulation of initial cell-material interaction (Tamada Y, Ikada Y. Effect of Preadsorbed Proteins on Cell Adhesion to Polymer Surfaces. Journal of Colloid and Interface Science 1993; 155(2):334-339 and Nuttelman C R, Mortisen D J, Henry S M, Anseth K S. Attachment of fibronectin to poly(vinyl alcohol) hydrogels promotes NIH3T3 cell adhesion, proliferation, and migration. J Biomed Mater Res 2001; 57(2):217-23). Wettability can change due to nanoroughness of the surface as well as due to the physicochemical changes induced due to graphene composite formation.

Moreover, electrical conductivity is desirable for myoblast growth and differentiation. Incorporation of graphene as an array is likely to improve the electrical conductivity of fibrous hydrogel scaffolds. As shown in FIG. 14 (K), graphene composite scaffolds show increased conductivity compared to 0% graphene scaffolds. Slight increase in the electrical current can be noticed for 0.1% graphene from 0% graphene scaffolds. 0.01% and 0.05% show even further increase in electrical current from cyclic voltammetry measurements. EIS spectra (FIG. 14 (L)) shows impedances across all graphene composite scaffolds, regardless of concentration, relative to 0% graphene scaffolds. This indicates that the graphene addition improves conductivity of the hydrogel. However, such increase was not observed beyond 0.05% graphene concentration. This could be due to the hydrophobicity of the graphene, which affects the swelling and morphology of the gel.

Uniaxial mechanical characterization of the graphene-CHT-GG composite scaffolds: Formation of the composite structures due to the underlying self-assembly between graphene-CHT and GG changes the mechanical properties of the scaffold. Representative stress vs. strain curves for 0% graphene (CHT-GG control) and three composite scaffolds are plotted in FIG. 15 (A). It can be noticed from the plot that the composite scaffolds showed similar elongation (in the range of 80-120%) which demonstrated their comparable ductility. However, 0.1% graphene scaffolds show less % strain compared to the rest of types of scaffolds.

Figure 15:
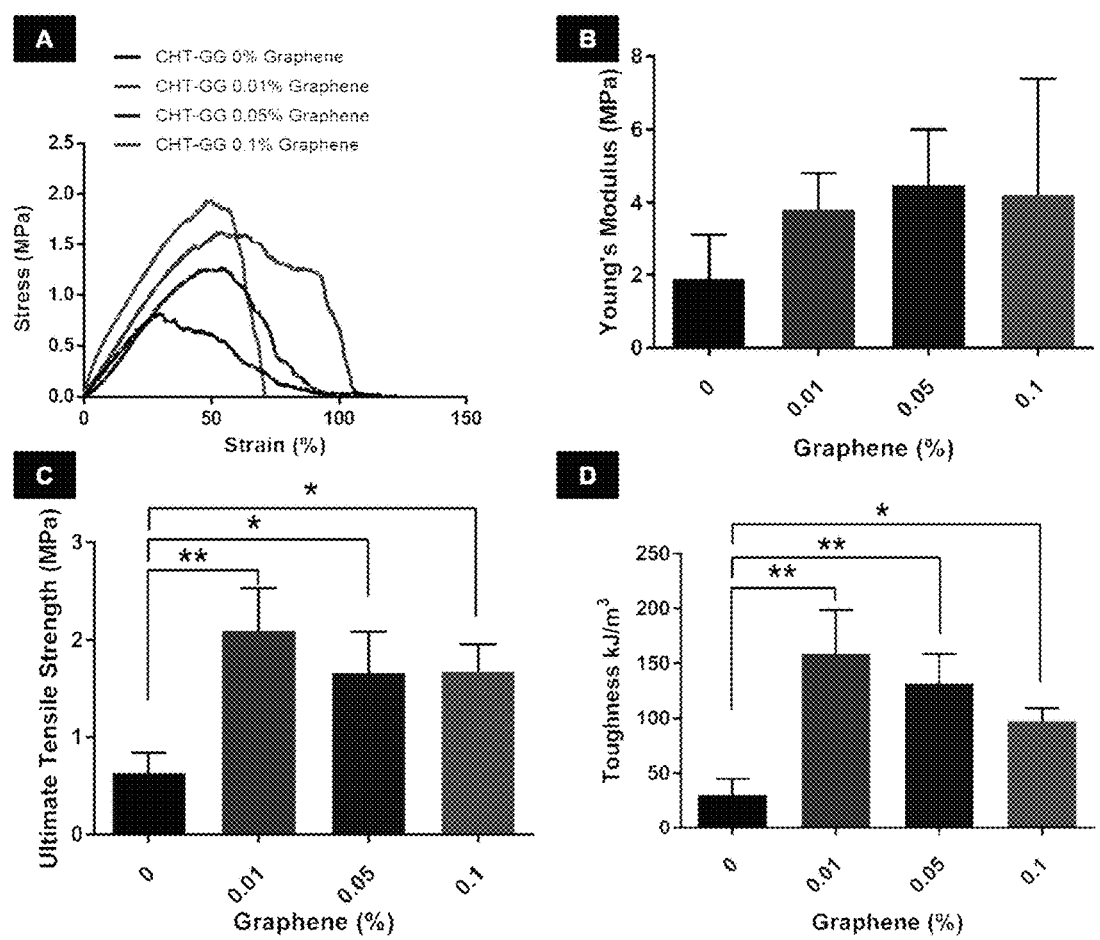
FIG. 15 shows uniaxial mechanical characterization of the graphene-CHT-GG composite scaffolds. Panel A shows representative stress-strain curves for different concentration of graphene in the composite scaffolds and control scaffold; Panel B shows average Young's modulus values for n=3 scaffolds per composite scaffold type; Panel C shows average Young's modulus values for n=3 scaffolds per composite scaffold type; Panel D shows average toughness values for n=3 scaffolds per composite scaffold type; Statistical significance was assessed by one-way ANOVA and Tukey post hoc test. * denotes $p<0.05$, ** denotes $p<0.005$.

Young's modulus was calculated as shown in FIG. 15 (B). Due to the variation among samples, statistical significance was not found by one-way ANOVA, however, a trend of increasing mean modulus can be seen with increase in graphene concentration up to 0.05% graphene scaffolds and reach plateau at 0.1% graphene scaffolds. It is important to retain the elasticity of hydrogel even with the graphene composite formation. Interestingly, calculation for Young's modulus indicates that the composite formation didn't significantly change the elastic properties.

Further, ultimate tensile strength (UTS) was calculated and plotted as seen in FIG. 15 (C). A statistically significant difference was found between 0% and three concentrations of graphene scaffolds. Moreover, there was no significant difference among 0.01%, 0.05% and 0.1% graphene scaffolds. It is desirable to improve tensile property of hydrogels for bearing the load at the damaged tissue area. Plot in FIG. 15 (C) shows a highly significant increase in UTS for all the types of graphene composite scaffolds suggesting that the composite formation significantly improved the self-assembly of the three components of the composite leading to an increase in the tensile strength of the scaffolds.

In order to study the resistance to of material fracture when stressed, toughness values were calculated from stress vs. strain curve. Three concentrations of graphene scaffolds showed significantly higher toughness than 0% graphene scaffolds. The trend among three concentration of graphene was the same as UTS and 0.01%, 0.05% and 0.1% graphene showed no statistical significance. Similar trend in the values of toughness indicates a significant improvement on energy dissipation leading to a sturdy yet elastic composite formation. Overall, uniaxial mechanical testing indicates improved stress bearing property in all graphene composite scaffolds.

Figure 16:
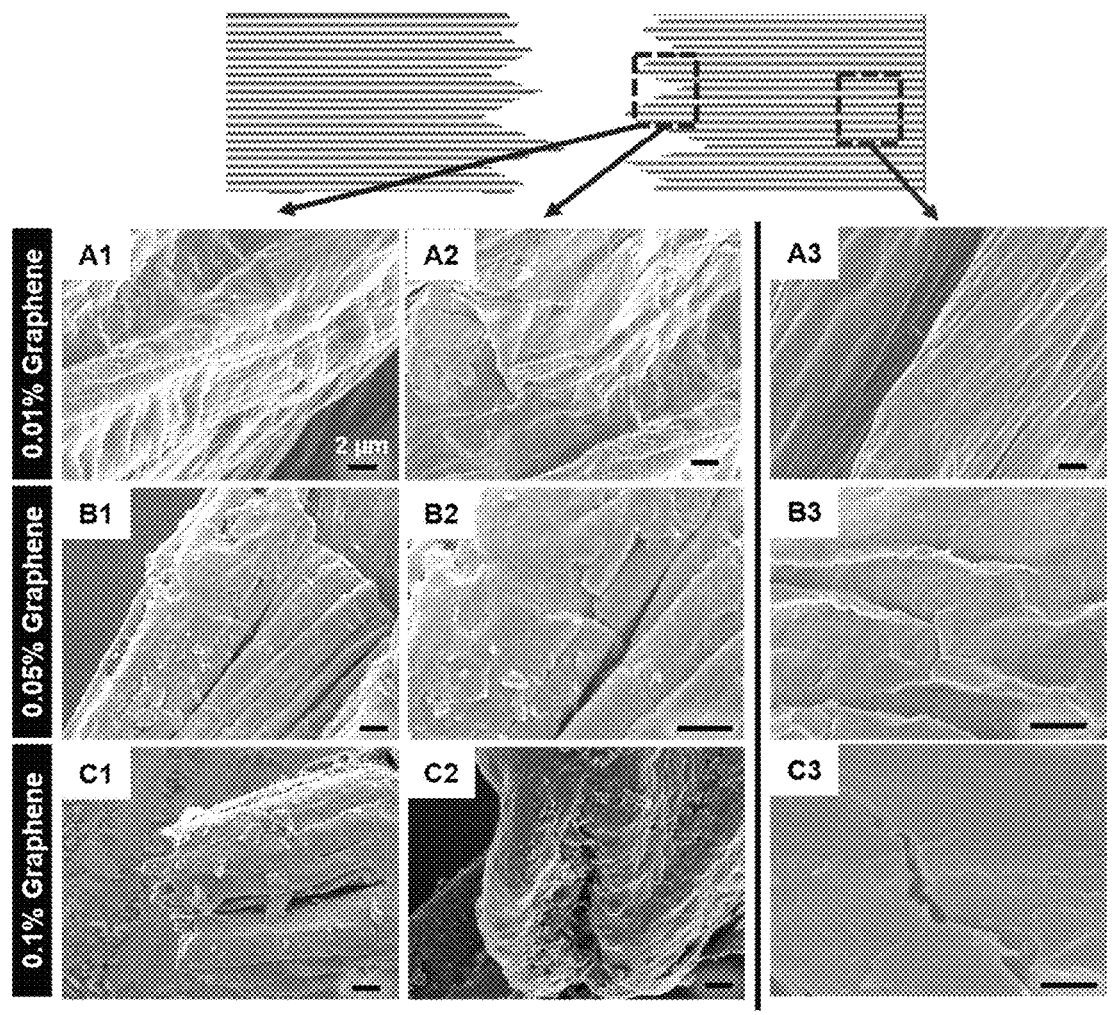
FIG. 16 shows scanning electron micrographs following fracture during uniaxial mechanical properties testing (top view). The schematic on the top of FIG. 16 indicates the areas near fracture point with red dotted boxes which corresponds to the SEM images numbered with 1 and 2, blue dotted box indicates farther to fracture area which corresponds to the SEM images numbered with 3; Panel A denotes 0.01% CHT-GG-graphene scaffolds, Panel B denotes 0.05% CHT-GG-graphene scaffolds; Panel C denotes 0.1% CHT-GG-graphene scaffolds; Scale bars represent 2 µm.

Following uniaxial tensile testing, fractured composite hydrogel samples were analyzed with SEM. Schematic in FIG. 16 shows the area of fractured scaffolds from which the image was acquired. Two different areas, i.e. near fracture point and farther to fracture point were chosen to analyze the stress distribution and effect of strain in the scaffolds. As shown in FIG. 16 (A1), 0.01% graphene scaffolds show creation of wavy wrinkles near fracture point. FIG. 16 (A2) shows graphene sheets on the surface near the wavy area. However, as the concentration of graphene increases to 0.05% and 0.1%, the scaffolds show flat, wrinkleless surfaces (FIG. 16 (B 1)). Magnified image of the same area shows brittle fracture with smooth edges (FIG. 16 (B2)). 0.1% graphene scaffold shows splintered fracture with sharp edges (FIG. 16 (C1)) whereas FIG. 16 (C2) shows fragments and flakes of the material created due the fracture. Further to investigate the response of material to strain and fracture, area farther to fracture (marked with blue dotted box in the schematic) was assessed. As shown in FIG. 16 (A3), 0.01% graphene scaffolds show no crack formation. Moreover, in the area farther to fracture point, fibrous structure of the composite scaffolds was found to be intact following fracture. However, 0.05% graphene composite scaffolds showed different response to application of strain. It showed multiple small cracks in the area farther to fracture point and flake formation near these tiny cracks as shown in FIG. 16 (B3). Such area in 0.1% graphene scaffold reveals larger and splintered and brittle crack as shown in FIG. 16 (C3). Overall, the morphological changes support and clarify the slight increase in UTS and toughness exhibited by 0.01% graphene scaffolds in FIGS. 15 (C) and (D), even though they were not statistically significant. Analysis of the SEM images from farther to fracture area clarified the mechanical behavior of these composites, wherein 0.01% graphene scaffolds (FIG. 16 (A3)) showed no crack formation and intact fibrous structure indicating its reconciling property. 0.05% and 0.1% graphene scaffolds showed multiple crack formation indicating decreased self-healing and increased brittleness. 0.01% graphene scaffolds showed interesting self-healing property and minimal damage to area farther to fracture suggesting that the application of higher strain than its capacity lead to only one fracture point.

Figure 17:
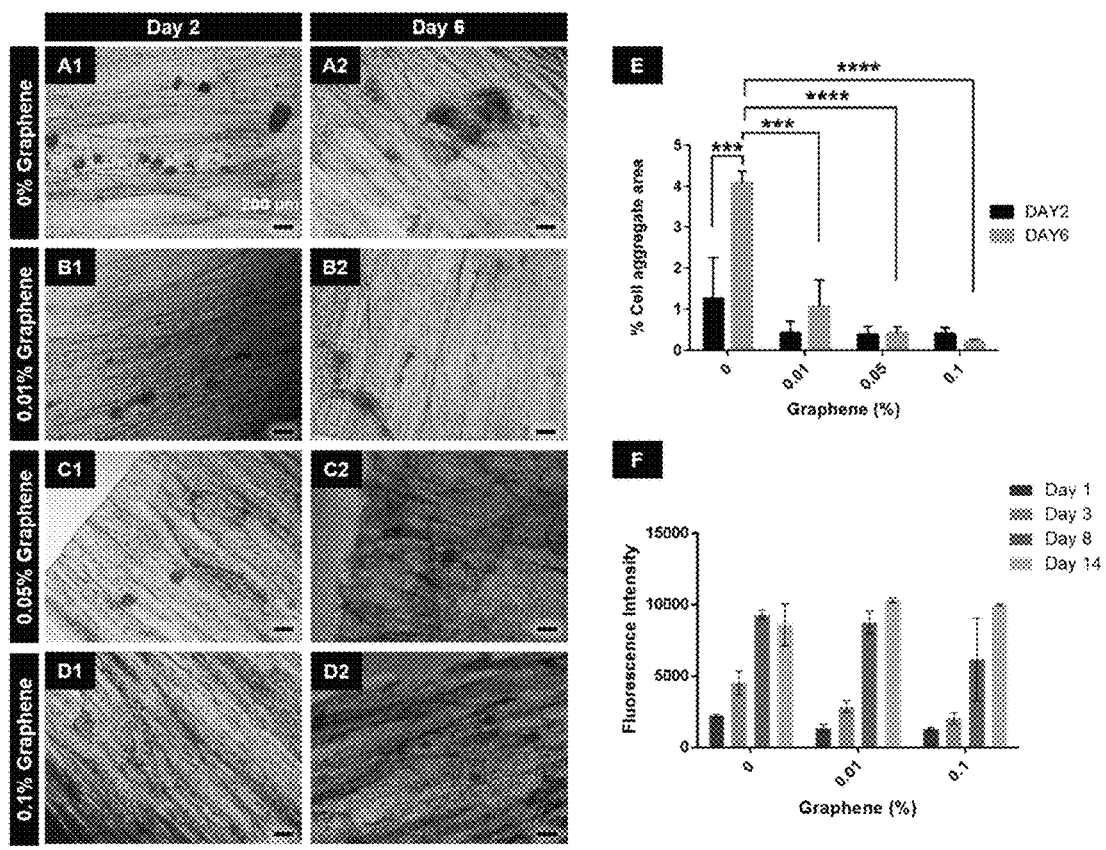
FIG. 17 shows cell spreading and cell metabolism on the composite scaffolds. Panels A1, B1, C1, and D1 represent cell aggregate formation in CHT-GG 0%, 0.01%, 0.05% and 0.1% graphene composite scaffolds, respectively, on day 2 after C2C12 cell seeding; and Panels A2, B2, C2, and D2 represent cell aggregate formation in CHT-GG 0%, 0.01%, 0.05% and 0.1% graphene composite scaffolds, respectively, on day 6 after C2C12 cell seeding, scale bars represent 200 µm, Panel E shows quantification of images acquired from n=3 samples of each type of scaffolds with at least 2 images. Area was calculated using ImageJ software; 0% control showed significant difference with all three concentration of the composite scaffolds on day 6; Panel F shows the metabolic activity of C2C12 cells over a period of 14 days. Both lower and higher concentration of graphene in composite scaffolds were found to be non-toxic for cells due to immobilization of graphene on the surface; statistical significance was tested by two-ANOVA and Tukey post hoc test for the multiple comparison. * denotes $p<0.0005$, ** denotes $p<0.0001$.

Spreading and metabolism of on the composite scaffolds: Significant improvement in wettability and electric conductivity are likely to have an effect on myoblast adhesion and spreading. Ability of graphene to promote cell-cell communication was checked by studying cell aggregate as shown in FIG. 17 (A1-D2). Cell aggregates were not observed on myoblast seeded scaffolds until two days of culturing in growth media (data not shown). 0% graphene (control) scaffolds showed multiple myoblast aggregates as visible in monochromatic light microscopic image at day 2 (FIG. 17 (A1)). Graphene composite scaffolds (FIG. 17 (B1), (C1), and (D1)) showed lesser aggregate areas compared to the 0%, graphene scaffolds at day 2. It can be noticed that 0.1% graphene scaffolds showed very less myoblast aggregates. The study was continued until day 6 in growth media and further images were acquired on day 6. As shown in FIG. 17 (A2), 0% graphene scaffolds showed fusion of the myoblast aggregates, leading to formation of a larger aggregate. However, graphene composite scaffolds showed minimal change in aggregate area from day 2 as shown in FIG. 17 (B2, C2, and D2). Further, to quantify the change in aggregate area to compare the samples in terms of time and graphene concentrations, image quantification was performed and % of cell aggregate area to total scaffold area was calculated. As shown in FIG. 17 (E), 0% graphene scaffolds showed highly significant increase in cell aggregate area after 4 days of culturing. None of the graphene scaffolds showed significant change in cell aggregate area during the same time. Moreover, all the graphene composite scaffolds showed significantly less % cell aggregate area than 0% graphene scaffolds. This is believed to be due to collective effect of increased nanoroughness, optimum wettability and improved electric conductivity, allowing myoblasts to communicate better. Similarly, Tang et al. designed a highly conductive graphene substrate to enhance cell-cell communication between neural stem cells (Tang M, et al. Enhancement of electrical signaling in neural networks on graphene films. Biomaterials 2013; 34(27):6402-6411). They observed a significant enhancement of neuron density with the use of graphene substrate.

In order to rule out the possibility that graphene slowed the proliferation of myoblasts, thereby leading to less cell aggregates as well as to assess the cytocompatibility of graphene composite scaffolds, AlamarBlue® assay was employed to assess the metabolic activity of myoblasts. It was performed on myoblast seeded scaffold for 14 days at regular interval. For feasibility, the lowest (0.01%) and the highest (0.1%) concentrations of graphene composites were considered along with 0% graphene control. All the scaffolds showed increase in metabolic activity as the time progressed (FIG. 17(F)). Graphene composite scaffolds showed similar cytocompatibility to that of graphene free scaffold with myoblast cells indicating the cytocompatibility of graphene sheets immobilized in the composite scaffolds.

Figure 18:
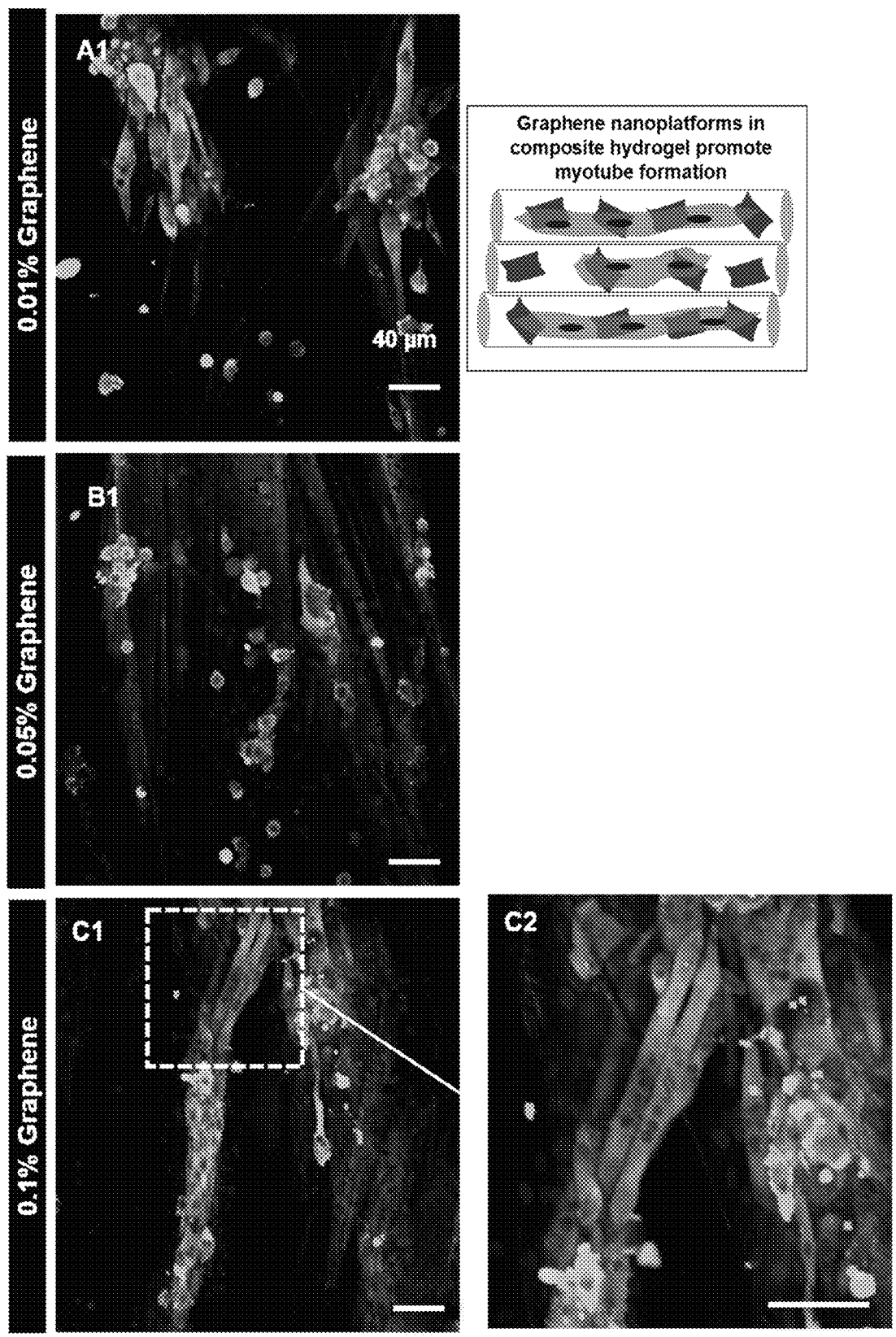
FIG. 18 shows differentiation of C2C12 myoblast into myotubes. The schematic in FIG. 18 shows the role of graphene nanoplatforms in facilitating myotube formation. C2C12 cells were seeded on the scaffolds and were allowed to proliferate for three days before switching to differentiation media culturing for 11 more days.

Differentiation of C2C12 myoblast into myotubes: Potential of biomaterial for skeletal muscle tissue engineering is assessed by formation of multinucleated myotubes from myoblasts. All the scaffolds (0% graphene control and graphene composites) showed the differentiation of myoblasts as shown in representative confocal images in FIG. 18. Scaffolds show immunofluorescence staining for DAPI and myosin heavy chain (MHC), which is a key marker for the differentiation of myoblasts into multinucleated myotubes for all types of scaffolds. Interestingly, composite scaffolds showed more number of nuclei per myotube indicating that graphene helped in the formation of denser myotube structures.

In sum, self-assembled graphene composite hydrogel scaffolds showed multiscale hierarchy and uniform distribution of graphene sheets. Addition of graphene significantly improved the mechanical properties such as UTS and toughness of the materials without changing elastic modulus. Graphene composite scaffolds with the least concentration of graphene showed uniform stress distribution as opposed to the higher concentration of the graphene composite scaffolds. Incorporation of graphene improved wettability, nano-roughness and electric conductivity. These changes facilitated better myoblast spreading, esp. for 0.1% w/v graphene scaffolds. Immobilization of graphene sheets in the hydrogel scaffolds prevented the possible toxic effect of graphene and showed cytocompatibility. Graphene composite scaffolds led to denser myotube formation. Overall, synergistic influence of fiber alignment, wettability and electric conductivity facilitate differentiation of myoblasts into multinucleated myotube along the direction of fibers.

The following clauses illustrate exemplary aspects of the invention:

1. A method of producing a biotherapeutic composition, comprising feeding a first component comprising a positively-charged polyelectrolyte, and a second component comprising a negatively-charged polyelectrolyte through a fluid flow passage to produce a product comprising a anisotropic structure.
2. The method of clause 1, wherein the passage is cylindrical, and is optionally a tube or a hypodermic needle.
3. The method of clause 1, wherein the passage has a largest cross section of 10 mm or less.
4. The method of clause 1, further comprising collecting the product onto a surface, and drying the collected material, e.g., to produce a sheet or other form.
5. The method of clause 1, wherein the negatively-charged polyelectrolyte and/or the positively-charged polyelectrolyte is a polysaccharide.
6. The method of any one of clauses 1-5, wherein the negatively-charged polyelectrolyte is one or more of gellan gum (GG) and alginate (Alg), Kappa carrageenan (KCa), hyaluronic acid (HA), chondroitin sulfate, poly(aspartic acid), and poly(glutamic acid) (PGA).
7. The method of any one of clauses 1-6, in which the positively-charged polyelectrolyte is chosen from one or more of: chitosan, glucosamine sulfate, chondroitin sulfate, or a positively-charged peptide.
8. The method of any one of clauses 1-5, wherein the positively-charged polyelectrolyte is poly-L-lysine, polycysteine, and poly-L-arginine.
9. The method of any one of clauses 1-5, wherein the positively-charged electrolyte is chitosan.
10. The method of clause 9, wherein the negatively-charged electrolyte is alginate, gellan gum, and/or kappa-carageenan.
11. The method of clause 1, wherein the positively-charged polyelectrolyte and/or the negatively-charged polyelectrolyte are a polyurethane, a polyester, or a polyether.
12. The method of any one of clauses 1-11, wherein the absolute values of the zeta potentials for the positively-charged polyelectrolyte and the negatively-charged polyelectrolyte differ by no more than 50%.
13. The method of any one of clauses 1-11, wherein the overall average charge of the positively-charged polyelectrolyte is less than the overall average charge of the negatively-charged polyelectrolyte, yielding a aligned structure having an overall negative charge.
14. The method of any one of clauses 1-13, further comprising feeding a cationic or anionic composition into the passage with the first and second components.
15. The method of clause 13, wherein the cationic or anionic composition comprises $Ca^{2+}$ and/or a calcium phosphate, such as hydroxyapatite.
16. The method of any one of clauses 1-15, further comprising feeding a therapeutic agent into the passage with the first and second components.
17. The method of clause 16, wherein the therapeutic agent is one or more of: an antimicrobial agent, a growth factor, a cytokine, an antioxidant, an anticancer agent, an anti-inflammatory agent, a retinoid, and a steroid.
18. The method of clause 16, wherein the therapeutic agent is: basic fibroblast growth factor (bFGF), acidic fibroblast growth factor (aFGF), vascular endothelial growth factor (VEGF), hepatocyte growth factor (HGF), insulin-like growth factors 1 and 2 (IGF-1 and IGF-2), platelet derived growth factor (PDGF), stromal derived factor 1 alpha (SDF-1 alpha), nerve growth factor (NGF), ciliary neurotrophic factor (CNTF), neurotrophin-3, neurotrophin-4, neurotrophin-5, pleiotrophin protein (neurite growth-promoting factor 1), midkine protein (neurite growth-promoting factor 2), brain-derived neurotrophic factor (BDNF), tumor angiogenesis factor (TAF), corticotrophin releasing factor (CRF), transforming growth factors α and β (TGF-α and TGF-β), interleukin-8 (IL-8), granulocyte-macrophage colony stimulating factor (GM-CSF), osteopontin, osteocalcin, an interleukin, and/or an interferon.
19. The method of clause 16, wherein the therapeutic agent is a biologic.
20. The method of any one of clauses 1-13, further comprising feeding a carbon allotrope into the passage with the first and second components.
21. The method of any one of clauses 1-20, in which one or both of the positively-charged polyelectrolyte and the negatively-charged polyelectrolyte is conjugated to a peptide, examples of which include, a peptide including or consisting of one or more of IKLLI (SEQ ID NO: 1) (anti-apoptotic), REDV (SEQ ID NO: 2), LDV, RGDSP (SEQ ID NO: 3), RGDV (SEQ ID NO: 4), LRGDN (SEQ ID NO: 5), RGDT (SEQ ID NO: 6), YIGSR (SEQ ID NO: 7), TTSWSQ (SEQ ID NO: 8), AEIDGIEL (SEQ ID NO: 9), WYRGRL (SEQ ID NO: 10), SIKVAVS (SEQ ID NO: 11). PDSGR (SEQ ID NO: 12), RNIAEIIKDI (SEQ ID NO: 13). DGEA (SEQ ID NO: 14), VTXG (SEQ ID NO: 15), PRRARV (SEQ ID NO: 16). YEKPGSPPREV-VPRPRPGV (SEQ ID NO: 17), RPSLAKKQRFRHRN-RKGYRSQRGHSRGR (SEQ ID NO: 18), RIQNLL-KITNLRIKFVK (SEQ ID NO: 19). RGD, IKVAV (SEQ ID NO: 20) and IKVAVS (SEQ ID NO: 21).
22. A composition comprising an anisotropic assembly of a positively-charged polyelectrolyte and a negatively-charged polyelectrolyte, optionally, having a light and dark banding pattern, such as a collagen-like banding pattern as found in collagen.
23. The composition of clause 22, wherein the negatively-charged polyelectrolyte and/or the positively-charged polyelectrolyte is a polysaccharide.
24. The composition of clause 22 or 23, wherein the negatively-charged polyelectrolyte is one or more of gellan gum (GG) and alginate (Alg), Kappa carrageenan (KCa), hyaluronic acid (HA), chondroitin sulfate, poly(aspartic acid), and poly(glutamic acid) (PGA).
25. The composition of any one of clauses 22-24, in which the positively-charged polyelectrolyte is chosen from one or more of: chitosan, glucosamine sulfate, chondroitin sulfate, or a positively-charged peptide.
26. The composition of clause 25, wherein the positively-charged polyelectrolyte is poly-L-lysine, polycysteine, and poly-L-arginine.
27. The composition of clause 22, wherein the positively-charged electrolyte is chitosan.
28. The composition of clause 27, wherein the negatively-charged electrolyte is alginate, gellan gum, and/or kappa-carageenan.
29. The composition of clause 22, wherein the positively-charged polyelectrolyte and/or the negatively-charged polyelectrolyte are a polyurethane, a polyester, or a polyether.
30. The composition of any one of clauses 22-29, wherein the absolute values of the zeta potentials for the positively-charged polyelectrolyte and the negatively-charged polyelectrolyte differ by no more than 50%.
31. The composition of any one of clauses 22-29, wherein the overall average charge of the positively-charged polyelectrolyte is less than the overall average charge of the negatively-charged polyelectrolyte, yielding a aligned structure having an overall negative charge.
32. The composition of clause 22, in which one or both of the positively-charged polyelectrolyte and the negatively-charged polyelectrolyte is conjugated to a peptide, examples of which include, a peptide including or consisting of one or more of IKLLI (SEQ ID NO: 1) (anti-apoptotic), REDV (SEQ ID NO: 2), LDV, RGDSP (SEQ ID NO: 3), RGDV (SEQ ID NO: 4), LRGDN (SEQ ID NO: 5), RGDT (SEQ ID NO: 6), YIGSR (SEQ ID NO: 7), TTSWSQ (SEQ ID NO: 8), AEIDGIEL (SEQ ID NO: 9). WYRGRL (SEQ ID NO: 10), SIKVAVS (SEQ ID NO: 11). PDSGR (SEQ ID NO: 12), RNIAEIIKDI (SEQ ID NO: 13). DGEA (SEQ ID NO: 14), VTXG (SEQ ID NO: 15), PRRARV (SEQ ID NO: 16), YEKPGSPPREV-VPRPRPGV (SEQ ID NO: 17). RPSLAKKQRFRHRN-RKGYRSQRGHSRGR (SEQ ID NO: 18), RIQNLL-KITNLRIKFVK (SEQ ID NO: 19), RGD, IKVAV (SEQ ID NO: 20) and IKVAVS (SEQ ID NO: 21).
33. The composition of any of clauses 22-32, complexed with a carbon allotrope.
34. The composition of any of clauses 22-32, complexed with a cationic composition.
35. The composition of clause 34, wherein the cationic composition comprises $Ca^{2+}$ and/or a calcium phosphate, such as hydroxyapatite.
36. The composition of any of clauses 22-32, complexed with a therapeutic agent.
37. The composition of clause 36, wherein the therapeutic agent is one or more of: an antimicrobial agent, a growth factor, a cytokine, an antioxidant, an anticancer agent, an anti-inflammatory agent, a retinoid, a biologic, and/or a steroid.
38. The composition of clause 37, wherein the therapeutic agent is: basic fibroblast growth factor (bFGF), acidic fibroblast growth factor (aFGF), vascular endothelial growth factor (VEGF), hepatocyte growth factor (HGF), insulin-like growth factors 1 and 2 (IGF-1 and IGF-2), platelet derived growth factor (PDGF), stromal derived factor 1 alpha (SDF-1 alpha), nerve growth factor (NGF), ciliary neurotrophic factor (CNTF), neurotrophin-3, neurotrophin-4, neurotrophin-5, pleiotrophin protein (neurite growth-promoting factor 1), midkine protein (neurite growth-promoting factor 2), brain-derived neurotrophic factor (BDNF), tumor angiogenesis factor (TAF), corticotrophin releasing factor (CRF), transforming growth factors α and β (TGF-α and TGF-β), interleukin-8 (IL-8), granulocyte-macrophage colony stimulating factor (GM-CSF), osteopontin, osteocalcin, an interleukin, and/or an interferon.
39. A method of producing a composition for use in bone mineralization, drug delivery, cell-growth and muscle tissue engineering, comprising:
   a. mixing a positively-charged polysaccharide and a negatively-charged polysaccharide to produce a mixture; and
   b. passing the mixture through a passage of sufficient diameter and length to produce an anisotropic product.
40. The method of clause 39, wherein the positively-charged polyelectrolyte is chosen from one or more of: chitosan, glucosamine sulfate, chondroitin sulfate, or a positively-charged peptide and/or the negatively-charged polyelectrolyte is one or more of gellan gum (GG) and alginate (Alg), Kappa carrageenan (KCa), hyaluronic acid (HA), chondroitin sulfate, poly(aspartic acid), and poly(glutamic acid) (PGA).
41. A method of delivering a therapeutic agent or cell to a patient, comprising administering to the patient a composition prepared by any one of clauses 16-21 or according to clauses 36-38 to a patient.
42. A method of growing cells or tissue, comprising incubating, in an appropriate cell growth medium, cells placed in contact with the composition prepared by any one of clauses 1-21 or according to clauses 22-39.
43. A method of making tissue, comprising implanting a composition according to any one of clauses 1-38 into a patient.
44. The method of clause 43, wherein the tissue is bone, nerve, or muscle.
45. The method of clause 43, wherein the tissue is nerve or muscle, and the method further comprises feeding a carbon allotrope into the passage with the first and second components.
46. The method of clause 43, further comprising feeding a therapeutic agent into the passage with the first and second components.

Having described this invention, it will be understood to those of ordinary skill in the art that the same can be performed within a wide and equivalent range of conditions, formulations and other parameters without affecting the scope of the invention or any embodiment thereof.

What is claimed is:

1. A method of producing a biotherapeutic composition, comprising feeding a first component comprising a positively-charged polyelectrolyte, and a second component comprising a negatively-charged polyelectrolyte through a fluid flow passage to produce a product comprising an anisotropic structure,
- wherein the method further comprises feeding a therapeutic agent into the passage with the first and second components, wherein the therapeutic agent is one or more of: basic fibroblast growth factor, acidic fibroblast growth factor, vascular endothelial growth factor, hepatocyte growth factor, insulin-like growth factors 1 and 2, platelet derived growth factor, stromal derived factor 1 alpha, nerve growth factor, ciliary neurotrophic factor, neurotrophin-3, neurotrophin-4, neurotrophin-5, pleiotrophin protein, midkine protein, brain-derived neurotrophic factor, tumor angiogenesis factor, corticotrophin releasing factor, transforming growth factors α and β, granulocyte-macrophage colony stimulating factor, osteopontin, osteocalcin, an interleukin, and/or an interferon, and
- wherein the positively-charged polyelectrolyte has a net positive zeta potential, and the negatively-charged polyelectrolyte has a net negative zeta potential.

2. The method of claim 1, wherein the passage is cylindrical.

3. The method of claim 1, wherein the passage has a largest cross section of 10 mm or less.

4. The method of claim 1, further comprising collecting the product onto a surface, and drying the collected material to produce a sheet or other form.

5. The method of claim 1, wherein the negatively-charged polyelectrolyte is one or more of gellan gum and alginate, Kappa carrageenan, hyaluronic acid, chondroitin sulfate, poly(aspartic acid), and poly(glutamic acid); and wherein the positively-charged polyelectrolyte is chosen from one or more of: chitosan, glucosamine sulfate, chondroitin sulfate, or a positively-charged peptide.

6. The method of claim 1, wherein the positively-charged electrolyte is chitosan and/or the negatively-charged electrolyte is alginate, gellan gum, and/or kappa-carageenan.

7. The method of claim 1, wherein the positively-charged polyelectrolyte and/or the negatively-charged polyelectrolyte are a polyurethane, a polyester, or a polyether.

8. The method of claim 1, further comprising feeding a cationic or anionic composition into the passage with the first and second components.

9. The method claim 1, further comprising feeding a carbon allotrope into the passage with the first and second components.

10. A composition comprising an anisotropic assembly of a positively-charged polyelectrolyte and a negatively-charged polyelectrolyte,
- wherein the composition is complexed with a therapeutic agent, and wherein the therapeutic agent is one or more of: basic fibroblast growth factor, acidic fibroblast growth factor, vascular endothelial growth factor, hepatocyte growth factor, insulin-like growth factors 1 and 2, platelet derived growth factor, stromal derived factor 1 alpha, nerve growth factor, ciliary neurotrophic factor, neurotrophin-3, neurotrophin-4, neurotrophin-5, pleiotrophin protein, midkine protein, brain-derived neurotrophic factor, tumor angiogenesis factor, corticotrophin releasing factor, transforming growth factors α and β, granulocyte-macrophage colony stimulating factor, osteopontin, osteocalcin, an interleukin, and/or an interferon, and
- wherein the positively-charged polyelectrolyte has a net positive zeta potential, and the negatively-charged polyelectrolyte has a net negative zeta potential.

11. The composition of claim 10, wherein the negatively-charged polyelectrolyte is one or more of gellan gum and alginate, Kappa carrageenan, hyaluronic acid, chondroitin sulfate, poly(aspartic acid), and poly(glutamic acid); and wherein the positively-charged polyelectrolyte is chosen from one or more of: chitosan, glucosamine sulfate, chondroitin sulfate, or a positively-charged peptide.

12. The composition of claim 10, wherein the positively-charged polyelectrolyte and/or the negatively-charged polyelectrolyte are a polyurethane, a polyester, or a polyether.

13. The composition of claim 12, in which one or both of the positively-charged polyelectrolyte and the negatively-charged polyelectrolyte is conjugated to a peptide, and wherein the peptide is one or more of IKLLI (SEQ ID NO: 1), REDV (SEQ ID NO: 2), LDV, RGDSP (SEQ ID NO: 3), RGDV (SEQ ID NO: 4), LRGDN (SEQ ID NO: 5), RGDT (SEQ ID NO: 6), YIGSR (SEQ ID NO: 7), TTSWSQ (SEQ ID NO: 8), AEIDGIEL (SEQ ID NO: 9), WYRGRL (SEQ ID NO: 10), SIKVAVS (SEQ ID NO: 11), PDSGR (SEQ ID NO: 12), RNIAEIIKDI (SEQ ID NO: 13), DGEA (SEQ ID NO: 14), VTXG (SEQ ID NO: 15), PRRARV (SEQ ID NO: 16), YEKPGSPPREVVPRPRPGV (SEQ ID NO: 17), RPSLAKKQRFRHRNRKGYRSQRGHSRGR (SEQ ID NO: 18), RIQNLLKITNLRIKFVK (SEQ ID NO: 19), RGD, IKVAV (SEQ ID NO: 20) and IKVAVS (SEQ ID NO: 21).

14. The composition of claim 10, complexed with a carbon allotrope.

15. The composition of claim 10, complexed with a cationic composition.

16. A method of delivering a therapeutic agent or cell to a patient, comprising administering to the patient the composition according to claim 10.

17. A method of growing cells or tissue, comprising incubating, in an appropriate cell growth medium, cells placed in contact with the composition according to claim 10.

18. A method of making tissue, comprising implanting a composition according to claim 10 into a patient.

19. The method of claim 18, wherein the tissue is nerve or muscle, and the composition further comprises a carbon allotrope.

20. The method of claim 18, wherein the composition further comprises a therapeutic agent.

21. The method of claim 5, wherein the positively-charged peptide is one or more of poly-L-lysine, polycysteine and poly-L-arginine.

22. The method of claim 8, wherein the cationic or anionic composition comprises $Ca^{2+}$ and/or a calcium phosphate.

23. The composition of claim 11, wherein the positively-charged peptide is one or more of poly-L-lysine, polycysteine and poly-L-arginine.

24. The composition of claim 15, wherein the cationic or anionic composition comprises $Ca^{2+}$ and/or a calcium phosphate.

* * * * *

UNITED STATES PATENT AND TRADEMARK OFFICE
CERTIFICATE OF CORRECTION

PATENT NO. : 10,307,513 B2
APPLICATION NO. : 15/179505
DATED : June 4, 2019
INVENTOR(S) : Shilpa Sant Page 1 of 1

It is certified that error appears in the above-identified patent and that said Letters Patent is hereby corrected as shown below:

In the Claims

Column 41, Line 42, Claim 6, delete "kappa-carageenan." and insert -- kappa-carrageenan. --

Column 41, Line 49, Claim 9, after "method" insert -- of --

Signed and Sealed this
Twenty-sixth Day of October, 2021

Drew Hirshfeld
*Performing the Functions and Duties of the*
*Under Secretary of Commerce for Intellectual Property and*
*Director of the United States Patent and Trademark Office*